United States Patent
Yamada et al.

(10) Patent No.: US 10,959,892 B2
(45) Date of Patent: Mar. 30, 2021

(54) MANAGEMENT DEVICE AND CONTROL DEVICE FOR AUTONOMOUS PATIENT TRANSPORTATION VEHICLE

(71) Applicant: Panasonic Intellectual Property Management Co., Ltd., Osaka (JP)

(72) Inventors: Takashi Yamada, Cupertino, CA (US); Atsunobu Kato, Cupertino, CA (US); Dongdong Wang, Cupertino, CA (US)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 243 days.

(21) Appl. No.: 15/470,177

(22) Filed: Mar. 27, 2017

(65) Prior Publication Data

US 2018/0259959 A1    Sep. 13, 2018

Related U.S. Application Data

(60) Provisional application No. 62/468,267, filed on Mar. 7, 2017.

(51) Int. Cl.
*A61G 5/04* (2013.01)
*A61G 5/10* (2006.01)
*G06Q 50/30* (2012.01)
*G06Q 10/06* (2012.01)
*G05D 1/02* (2020.01)

(52) U.S. Cl.
CPC ............ *A61G 5/04* (2013.01); *A61G 5/10* (2013.01); *G05D 1/0282* (2013.01); *G06Q 10/0631* (2013.01); *G06Q 50/30* (2013.01); *A61G 2203/20* (2013.01); *A61G 2203/30* (2013.01); *A61G 2203/72* (2013.01); *G05D 2201/0206* (2013.01)

(58) Field of Classification Search
None
See application file for complete search history.

(56) References Cited

U.S. PATENT DOCUMENTS 5,455,621 A    10/1995  Morimura
10,137,047 B1*  11/2018  DiFrancesco ......... B64C 39/024
(Continued)

FOREIGN PATENT DOCUMENTS

| JP | H06-141229 A | 5/1994 |
| JP | 09-280878 A | 10/1997 |
| JP | 2000-113044 A | 4/2000 |

OTHER PUBLICATIONS

Office Action issued in corresponding Japanese Patent Application No. 2017-247792, dated Nov. 22, 2018, with English translation.

*Primary Examiner* — Navid Ziaeianmehdizadeh
(74) *Attorney, Agent, or Firm* — McDermott Will & Emery LLP

(57) ABSTRACT

A management device, comprising a controller that controls communication between a movable first terminal device and a second terminal device in which a moving range is narrower than the first terminal device, and a detector that detects that the first terminal device arrives at a target point by movement, wherein in a case where the detector detects the arrival at the target point, the controller ends the communication between the first terminal device and the second terminal device.

18 Claims, 16 Drawing Sheets

(56) References Cited

U.S. PATENT DOCUMENTS

| | | | |
|---|---|---|---|
| 2007/0255115 A1* | 11/2007 | Anglin, Jr. | G06F 19/3418 600/300 |
| 2012/0313775 A1* | 12/2012 | Davis | G01C 21/206 340/539.12 |
| 2014/0361871 A1* | 12/2014 | Silva | A61B 5/04012 340/5.52 |
| 2016/0001781 A1* | 1/2016 | Fung | B60W 40/08 701/36 |
| 2017/0266069 A1* | 9/2017 | Lozano | G05D 1/0212 |
| 2018/0120860 A1* | 5/2018 | Longin | A61G 5/0866 |

* cited by examiner

MANAGEMENT DEVICE AND CONTROL DEVICE FOR AUTONOMOUS PATIENT TRANSPORTATION VEHICLE

BACKGROUND OF THE INVENTION

1. Field of the Invention

The present invention relates to a control technique and especially relates to a management device and a control device to automatically move a vehicle.

2. Description of the Related Art

A medical examination order waiting system disposed in a hospital registers and displays an examination reception and an examination order. Generally, a patient for a follow-up examination waits to be called in a waiting room located in front of an examination room after the examination reception. A patient who receives a plurality of medical examinations knows his/her examination order on such as an order display for each section and moves to a corresponding examination room. To simplify movement of a patient having a disorder, an electric wheelchair is included in such the examination order waiting system. The electric wheelchair includes an I/F means, a transmission/reception control means, and a display means. The I/F means corresponds with examination reception data of an examination card. The transmission/reception control means sends and receives the examination reception data and examination order data to and from the examination management server. The display means displays and outputs the received examination order data (for example, refer to JP 2000-113044 A).

[Patent Literature 1] JP 2000-113044 A

SUMMARY OF THE INVENTION

A patient is seated on an electric wheelchair is automatically carried to a desired examination room. With respect to such a patient, a stay time in a hospital can be shortened by shortening a waiting time for an examination and an examination time.

The present invention is in view of the above state. An object of the present invention is to provide a technique to shorten a stay time.

To solve the above issue, a management device according to an embodiment of the present invention includes a controller and a detector. The controller controls a communication between a movable first terminal device and a second terminal device in which a moving range is narrower than the first terminal device. The detector detects that the first terminal device arrives at a target point by movement. The controller ends the communication between the first terminal device and the second terminal device in the case where the detector detects arrival at the target point.

Another embodiment of the present invention is a control device. The control device includes a first receiver, a second receiver, and a controller. The first receiver receives a stop instruction during automatic traveling of a vehicle toward a target point. The second receiver receives an instruction to restart automatic traveling of the vehicle after the first receiver has received the stop instruction. The controller stops automatic traveling of the vehicle when the first receiver receives the stop instruction and restarts automatic traveling of the vehicle when the second receiver receives the restart instruction. The controller (1) stops automatic traveling of a vehicle toward a target point in a case where the first receiver also receives a standby instruction after receiving a stop instruction, and the second receiver does not receive a restart instruction during a first period, and (2) stops automatic traveling of the vehicle toward a target point in a case where the first receiver does not receive a standby instruction after receiving a stop instruction, and the second receiver does not receive a restart instruction during a second period. In the controller, the first period is longer than the second period.

Another embodiment of the present invention is a management device. The management device includes a storage and a controller. The storage stores a corresponding relation between a riding point of a passenger and identification information of the passenger. The controller causes a first vehicle carrying the passenger to automatically travel along a forward path from the riding point to a target point and causes a second vehicle carrying the passenger to automatically travel along a return path. The controller acquires the riding point of a passenger from the corresponding relation stored in the storage based on the identification information of a passenger and sets the acquired riding point as an alighting point on the return path.

Further, another embodiment of the present invention is a control device. The control device includes setting unit, a controller, and a receiver. The setting unit sets a plurality of target point candidates. The controller causes a vehicle to automatically travel along a common path to a plurality of the target point candidates set by the setting unit. The receiver receives an instruction to select a target point from any of a plurality of the target point candidates set by the setting unit while the controller causes the vehicle to automatically travel. The controller causes the vehicle to automatically travel along a path to the selected target point in the case where the receiver receives the instruction.

Further, another embodiment of the present invention is also a control device. The control device includes a controller and a communication unit. The controller automatically drives a vehicle. The communication unit communicates information on a passenger riding in the vehicle while the controller causes the vehicle to automatically travel.

An arbitrary combination of the above-described components and expression of the present invention converted into a method, a device, a system, a storage medium, and a computer program are effective as an aspect of the present invention.

According to the present invention, a stay time can be shortened.

DETAILED DESCRIPTION OF THE INVENTION

A summary of the present invention will be described before the present invention is specifically described. An embodiment relates to an automatic carrier system provided in a hospital. An example of the automatic carrier system includes a vehicle which can automatically travel. The vehicle travels toward such as an examination room, an inspection room, and a medicine room in a hospital depending on a patient riding in the vehicle. As described above, it is desired to shorten patients' stay time in a hospital by such the automatic carrier system. In the embodiment, a movement time of a patient is effectively used to shorten a stay time of the patient in a hospital. For example, during movement, an examination is received, and a part of the examination is performed.

Here, regarding the automatic carrier system, (1) an overall configuration will be described first, and (2) a specific processing will be described next. Further, a moving flow in the case where patient arrives at a hospital, moves to an examination room, an inspection room, and a medicine room in a hospital, and leaves from the hospital will be assumed in (2) the specific processing. Therefore, in (2) the specific processing, (2.1) calling processing, (2.2) forward path moving processing, (2.3) movement stop processing, (2.4) examination processing during movement, (2.5) moving processing on the way, and (2.6) return path moving processing will be described in this order. A flow in a hospital is not limited thereto, and therefore a part of (2.1) to (2.6) may be omitted, and an order may be changed. Further, processing other than (2.1) to (2.6) may be added.

(1) Overall Configuration

Figure 1:
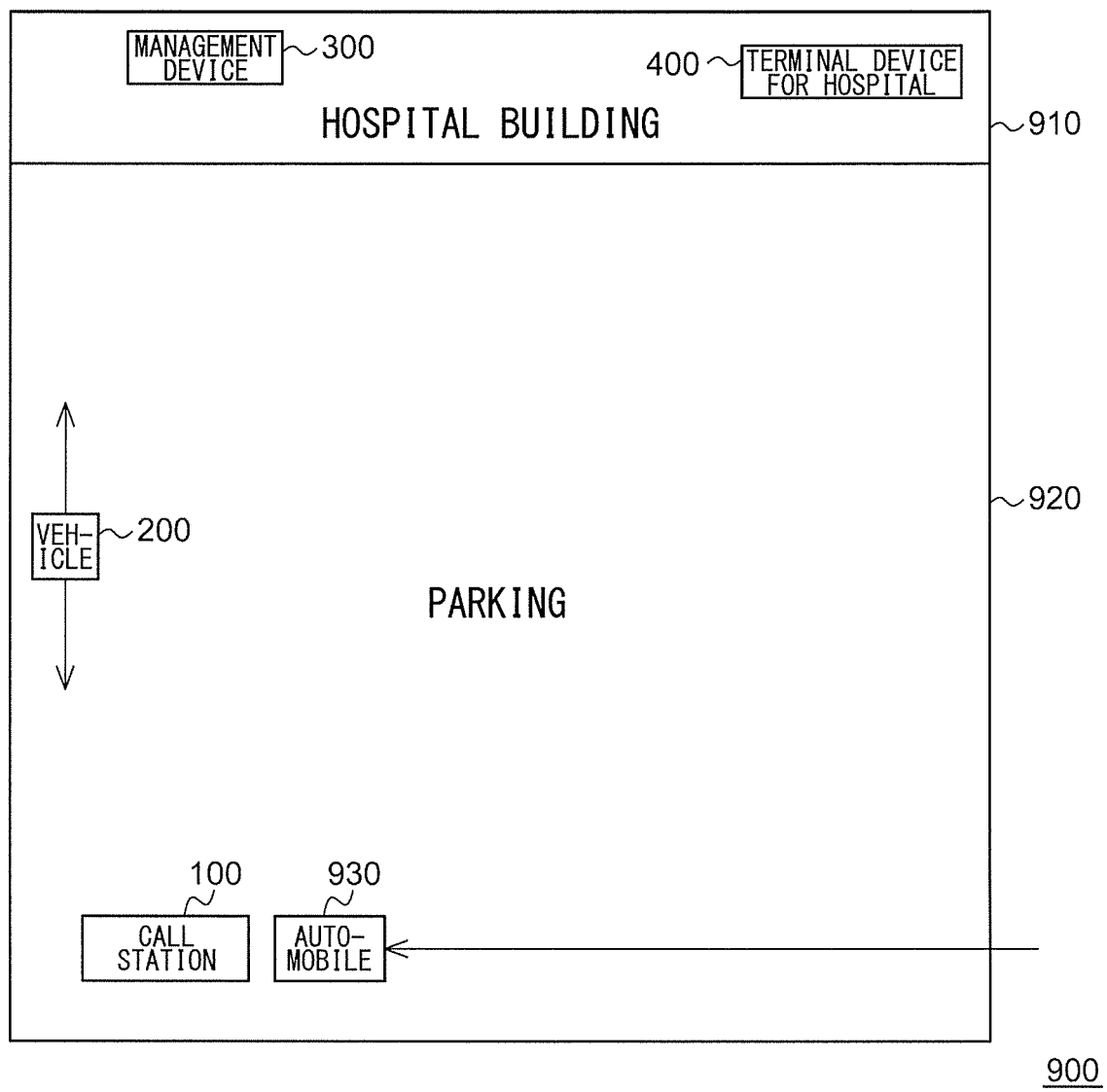
FIG. 1 is a view illustrating a layout in a hospital according to an embodiment.

FIG. 1 illustrates a layout in a hospital 900 according to an embodiment. The hospital 900 includes a hospital building 910 and a parking 920. The hospital building 910 includes a plurality of rooms including an examination room, an inspection room, a medicine room in a hospital, and a room for cash payment. A terminal device 400 for a hospital is disposed in each of the rooms. Therefore, a plurality of the terminal device 400 for a hospital is disposed in the hospital building 910. The terminal device 400 for a hospital is an electronic device operated by, for example, a doctor in an examination room, a laboratory technician in an inspection room, and a pharmacist in a medicine room in a hospital. An example of the terminal device 400 for a hospital includes a personal computer (PC) and may include a different interface by a doctor, a laboratory technician, and a pharmacist who operate the device. In addition, a management device 300 is also disposed in the hospital building 910. The management device 300 is connected to a plurality of the terminal devices 400 for a hospital as described later and corresponds to a server. The management device 300 performs each processing in an automatic carrier system, and the processing will be described later.

The parking 920 is provided adjacent to the hospital building 910, and a plurality of automobiles 930 can be parked. The automobiles 930 carry patients who visit the hospital 900 and are parked in the parking 920. A call station 100 is provided in the parking 920. The call station 100 is provided to call a vehicle 200 to be used when a patient who gets off from the automobile 930 parked in the parking 920 moves in the hospital building 910. One call station 100 is illustrated in FIG. 1. However, a plurality of the call stations 100 is disposed in the parking 920. Further, one vehicle 200 is illustrated in FIG. 1. However, a plurality of the vehicles 200 may be included. The vehicle 200 called by the call station 100 can be automatically operated and automatically travels. The vehicle 200 and the call station 100 are connected via the management device 300, and a call from the call station 100 is received by the vehicle 200 via the management device 300. The vehicle 200 carries a patient from near the call station 100 in accordance with an instruction from the management device 300 and travels toward such as an examination room.

According to the embodiment, a position of the call station 100 where a patient who arrives at the hospital 900 rides in the vehicle 200 is called "a riding point". Further, a room where a patient riding in the vehicle 200 moves to in the hospital building 910 is called "a target point". In the case where a patient moves to an examination room, an inspection room, and a medicine room in a hospital, a plurality of target points is set. Further, a position of the call station 100 at which a patient riding in the vehicle 200 gets off the vehicle 200 to return to the automobile 930 parked in the parking 920 is called "an alighting point". Here, the alighting point and the riding point are the same. Further, a path from the riding point to any of target points is called "a forward path", and a path from any of the target points to the alighting point is called "a return path". A target point on the forward path and a target point on the return path may be different.

Figure 2:
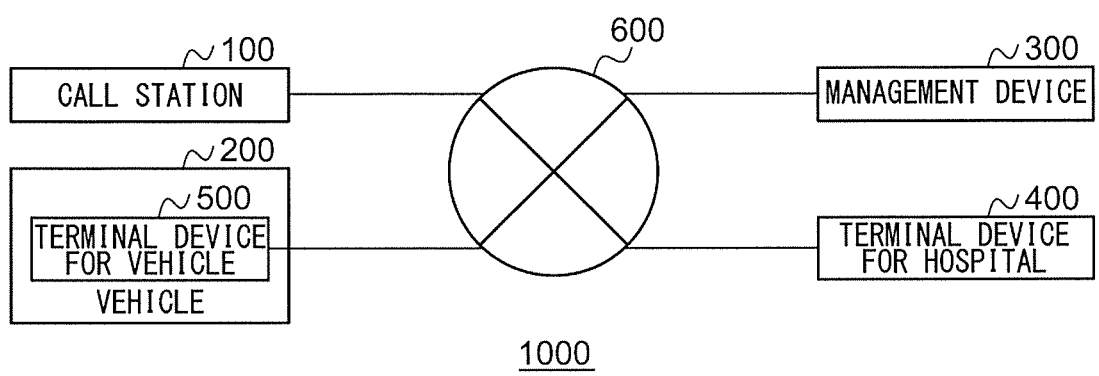
FIG. 2 is a diagram illustrating a configuration of an automatic carrier system according to the embodiment.

FIG. 2 illustrates a configuration of an automatic carrier system 1000 according to an embodiment. The automatic carrier system 1000 includes the call station 100, the vehicle 200, the management device 300, the terminal device 400 for a hospital, a terminal device 500 for a vehicle, and a network 600. The terminal device 500 for a vehicle is mounted in the vehicle 200 and can be moved with the vehicle 200. The terminal device 500 for a vehicle is used by a patient riding in the vehicle 200. On the other hand, the terminal device 400 for a hospital is disposed in rooms in the hospital building 910 as described above. Therefore, a moving range of the terminal device 400 is narrower than a moving range of the terminal device 500 for a vehicle. Here, an idea that "the moving range is narrow" includes no moving, and the terminal device 400 for a hospital having a narrow moving range may be a terminal device which is not moved, such as a stationary terminal device. The terminal device 400 for a hospital is used by such as a doctor in an examination room, a laboratory technician in an inspection room, and a pharmacist in a medicine room in a hospital. The call station 100 and the management device 300 are as described above.

The call station 100, the management device 300, the terminal device 400 for a hospital, the terminal device 500 for a vehicle are connected via the network 600 and can be communicated each other. The network 600 is combined with wireless networks and wired networks. The terminal device 500 for a vehicle is connected by the wireless network. The vehicle 200 is not directly connected to the network 600 and is communicated via the terminal device 500 for a vehicle. However, to clarify a description, it may be described below that the vehicle 200 can perform communication.

Figure 3A:
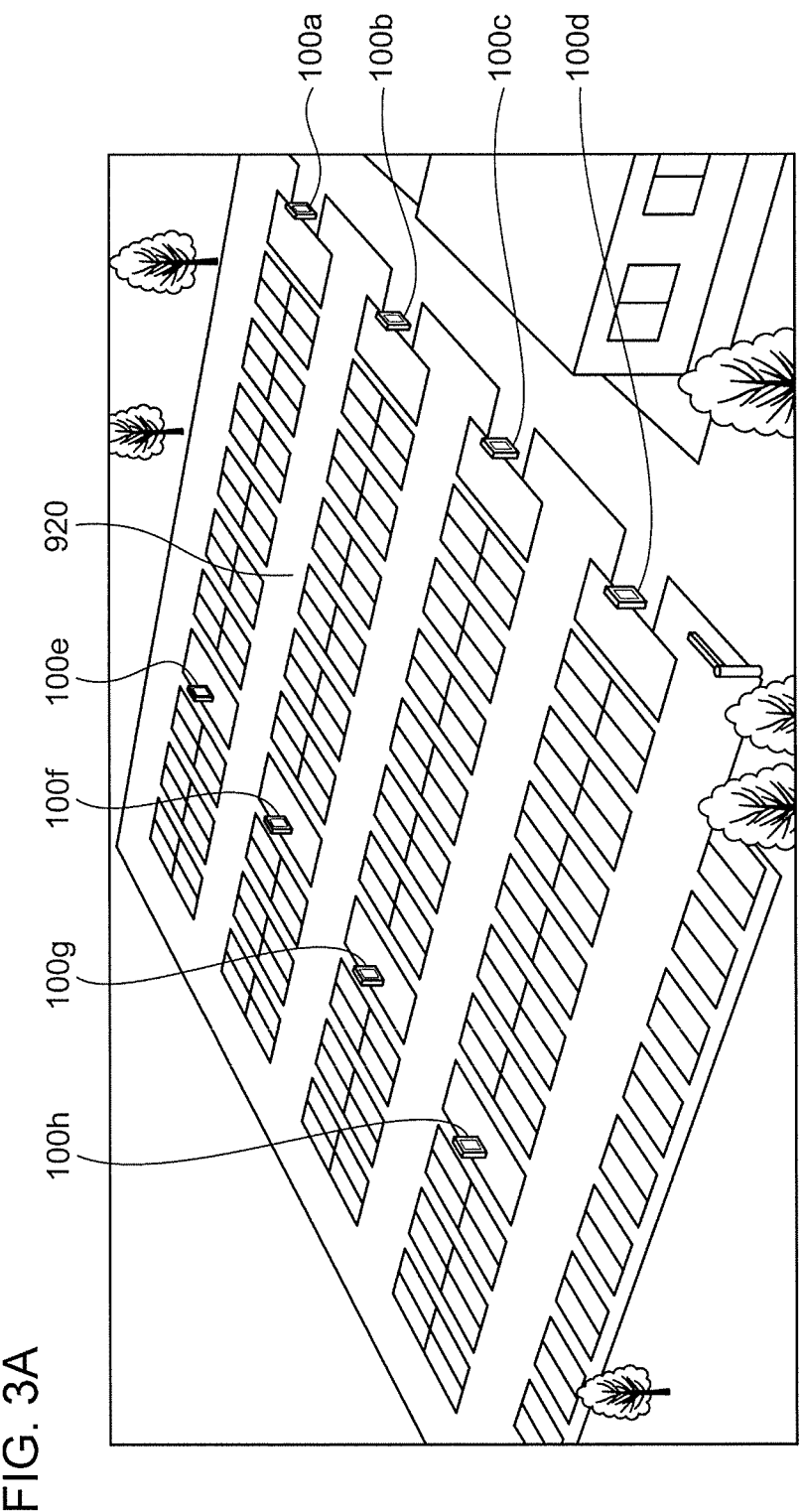
FIGS. 3A and 3B are views illustrating a layout and a structure of a call station described in FIG. 2.
Figure 3B:
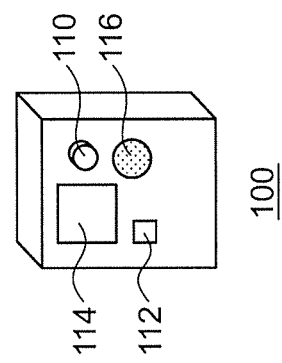

FIGS. 3A and 3B are views illustrating a layout and a structure of the call station 100. FIG. 3A illustrates a plurality of the call stations 100 disposed in the parking 920. Here, "eight" call stations 100 including a first call station 100a to an eighth call station 100h are disposed. A number of the call stations 100 is not limited to "eight". Each call station 100 is disposed so as to be scattered in the parking 920.

FIG. 3B is a perspective view illustrating a structure of the call station 100. The call station 100 includes a button 110, an ID reader 112, a display unit 114, and a speaker 116. The button 110 is pushed in the case where a patient calls the vehicle 200. A guidance and an instruction for a patient are displayed by the display unit 114, and the speaker 116 outputs the guideline and the instruction with voice to the patient. The ID reader 112 reads a patient identification (ID) input by a patient. The patient ID is information to identify a patient.

Figure 4:
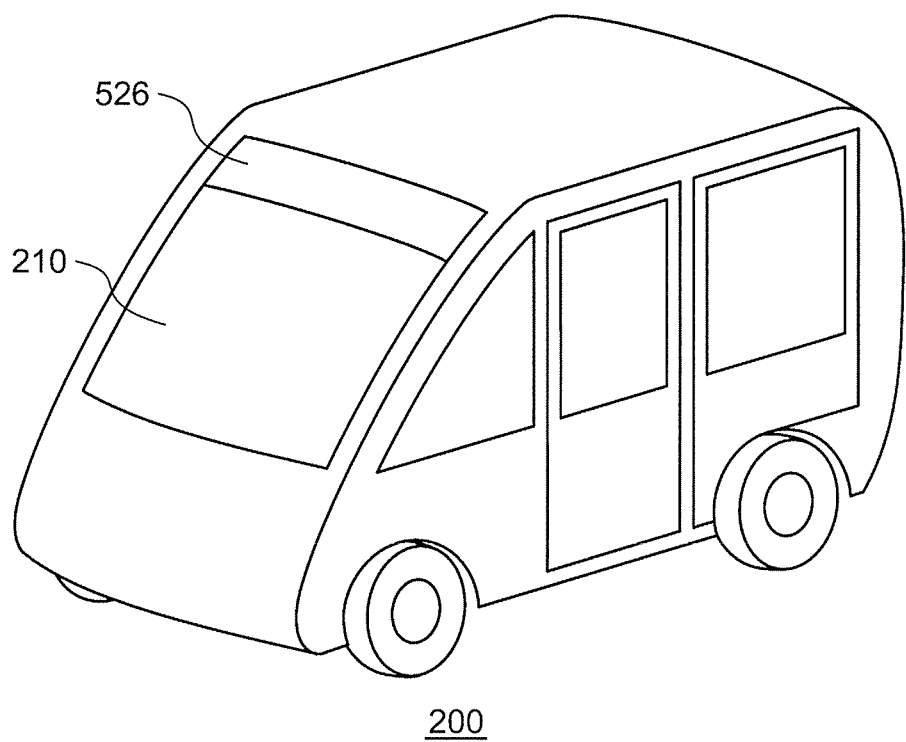
FIG. 4 is a perspective view illustrating a structure of a vehicle described in FIG. 2.

FIG. 4 is a perspective view illustrating a structure of the vehicle 200. The vehicle 200 includes a wind shield 210 on a front side and includes a vehicle exterior monitor 526 on an upper side of the wind shield 210. The vehicle exterior monitor 526 indicates information to specify a patient, including a name and an ID of the patient. An appearance of the vehicle 200 is not limited to FIG. 4.

Figure 5:
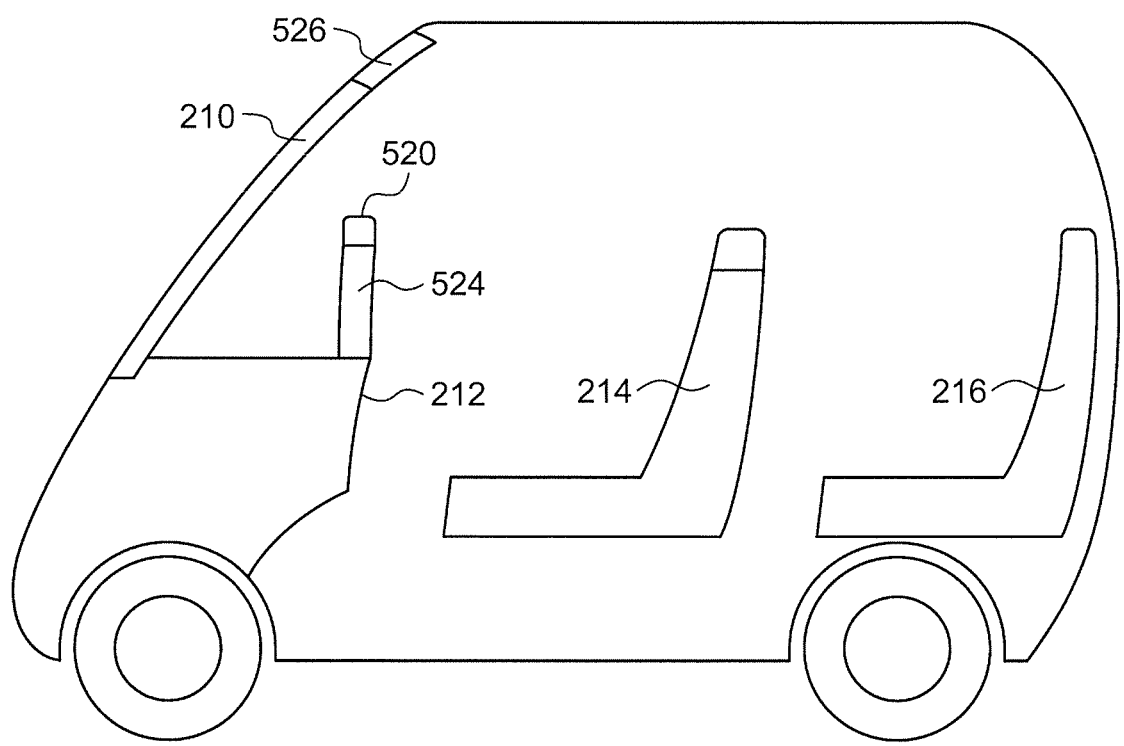
FIG. 5 is a perspective view illustrating a structure of a vehicle described in FIG. 4.

FIG. 5 is a sectional view illustrating a structure of the vehicle 200. As described above, the wind shield 210, the vehicle exterior monitor 526 are disposed on a front side, and a dashboard 212 is disposed on a rear side thereof. Further, an in-vehicle monitor 524 and a camera 520 are disposed on an upper side of the dashboard 212. Furthermore, a front seat 214 and a rear seat 216 are disposed in this order toward a rear side from the dashboard 212. For example, a patient is seated on the front seat 214.

Figure 6:
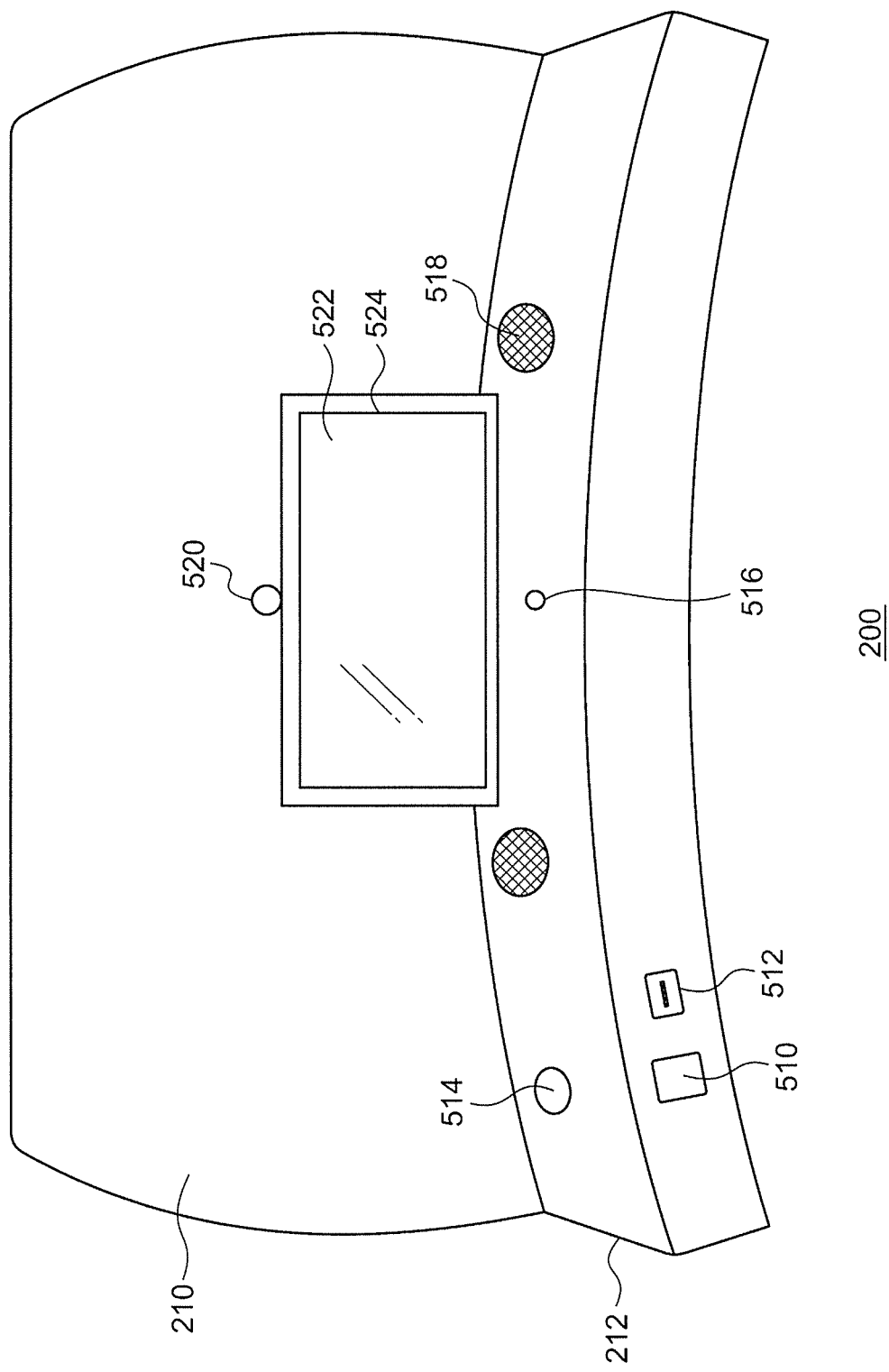
FIG. 6 is a view illustrating a structure in the vehicle described in FIG. 4.

FIG. 6 illustrates an inner structure of the vehicle 200. The wind shield 210 is disposed on a front side of the dashboard 212 disposed on a front side of a cabin. An ID reader 510, a card reader 512, a hold button 514 are disposed on a left side of the dashboard 212. The ID reader 510, the card reader 512, and the hold button 514 are disposed on a right side of the dashboard 212. The in-vehicle monitor 524 is disposed at a center of the dashboard 212. The in-vehicle monitor 524 includes a touch panel display and therefore may be called an input unit 522. A microphone 516 is disposed on a lower side of the in-vehicle monitor 524. A speaker 518 is disposed on both sides of the in-vehicle monitor 524. The camera 520 is disposed on an upper side of the in-vehicle monitor 524.

(2) Specific Processing

Figure 7:
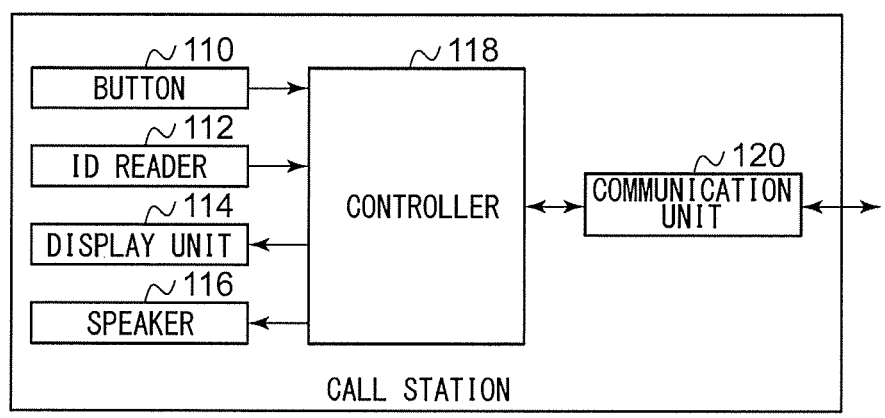
FIG. 7 is a view illustrating a configuration of the call station described in FIG. 2.
Figure 8:
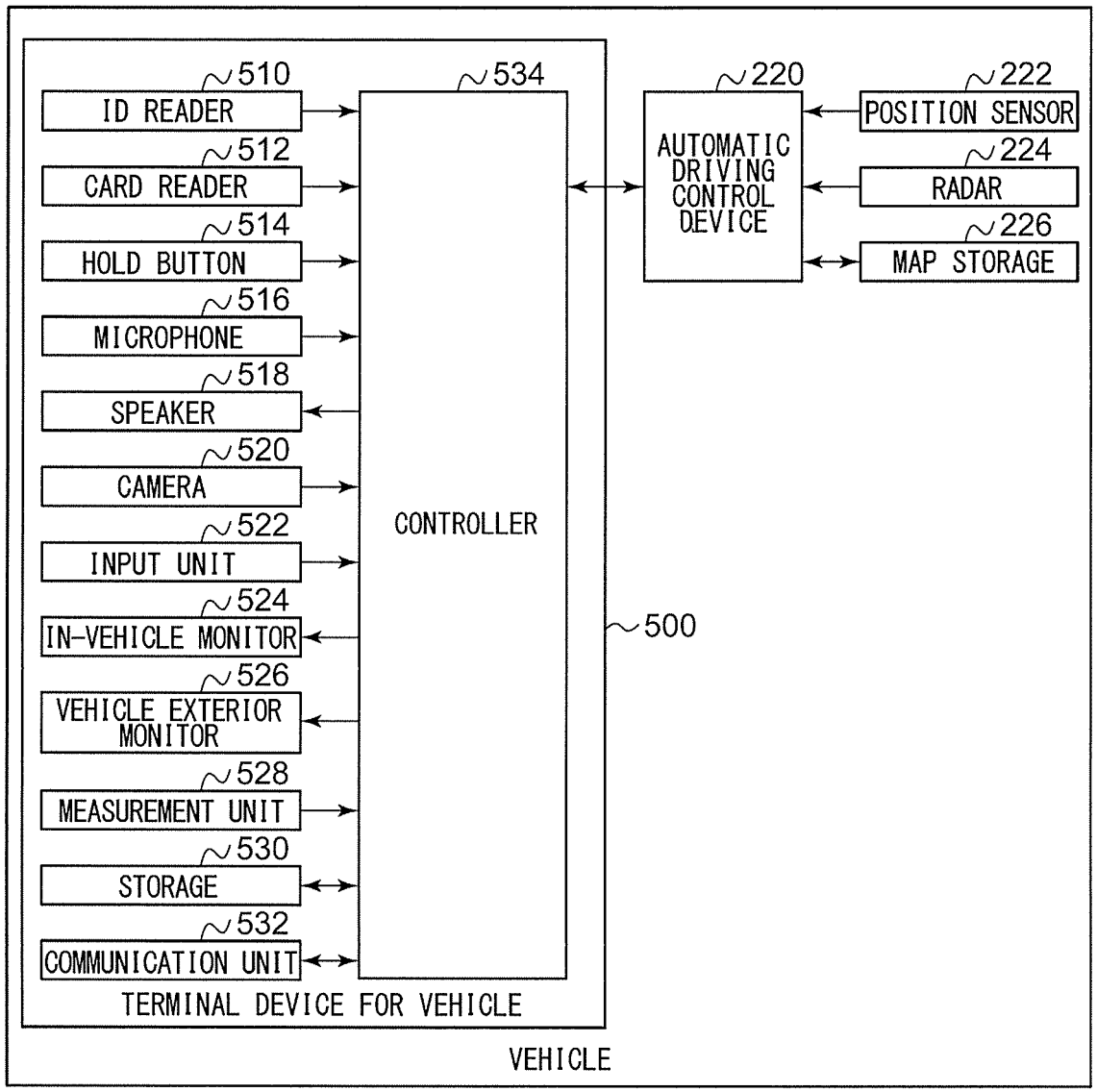
FIG. 8 is a view illustrating a configuration of the vehicle described in FIG. 2.
Figure 10:
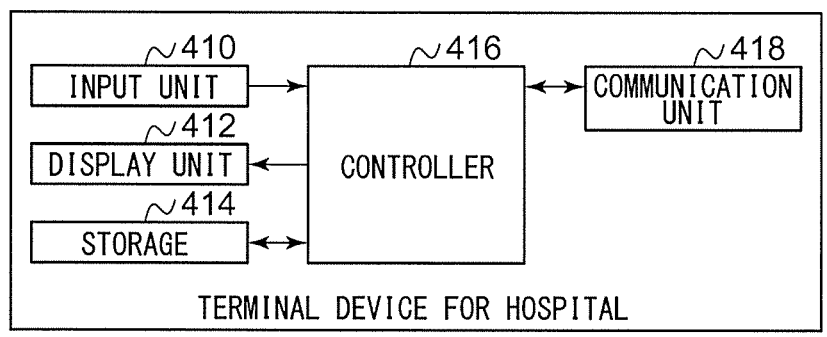
FIG. 10 is a view illustrating a configuration of a terminal device for a hospital described in FIG. 2.

FIGS. 7 and 10 illustrate configurations of the call station 100, the vehicle 200, the management device 300, and the terminal device 400 for a hospital, which are included in the automatic carrier system 1000. FIG. 7 illustrates a configuration of the call station 100. The call station 100 includes the button 110, the ID reader 112, the display unit 114, the speaker 116, a controller 118, and a communication unit 120. FIG. 8 illustrates a configuration of the vehicle 200. The vehicle 200 includes an automatic driving control device 220, a position sensor 222, a radar 224, a map storage 226, and the terminal device 500 for a vehicle. The terminal device 500 for a vehicle includes the ID reader 510, the card reader 512, the hold button 514, the microphone 516, the speaker 518, the camera 520, the input unit 522, the in-vehicle monitor 524, the vehicle exterior monitor 526, a measurement unit 528, a storage 530, a communication unit 532, and a controller 534.

Figure 9:
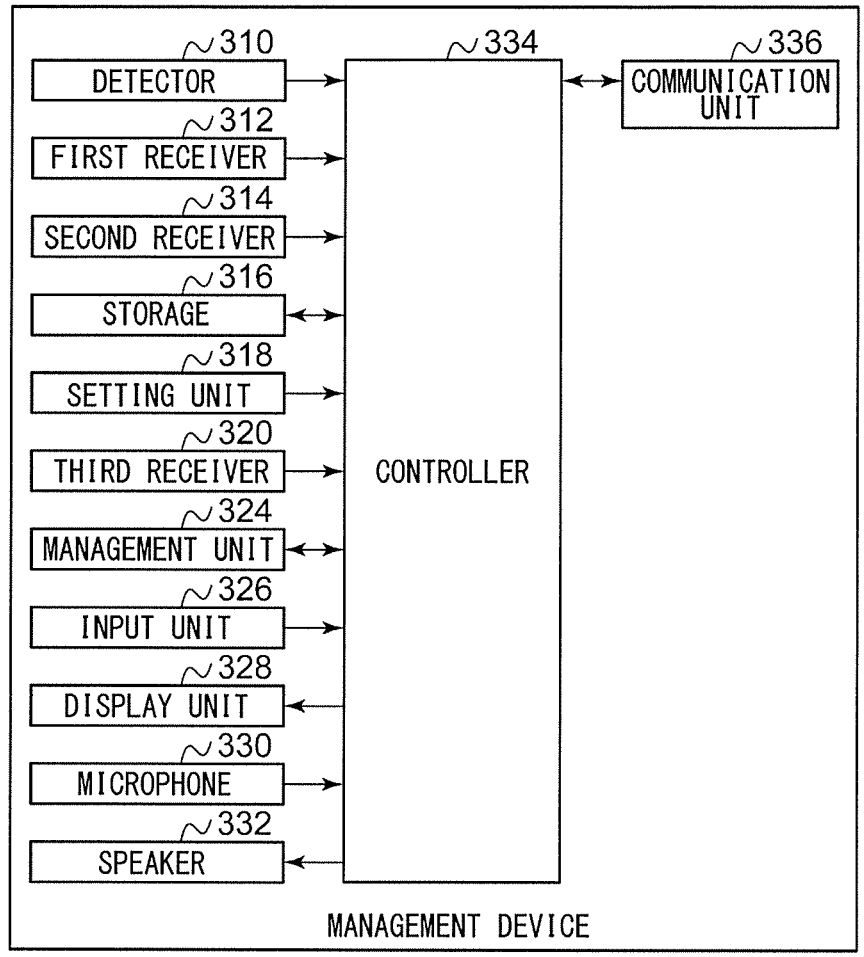
FIG. 9 is a view illustrating a configuration of a management device described in FIG. 2.

FIG. 9 illustrates a configuration of the management device 300. The management device 300 includes a detector 310, a first receiver 312, a second receiver 314, a storage 316, a setting unit 318, a third receiver 320, a management unit 324, an input unit 326, a display unit 328, a microphone 330, a speaker 332, a controller 334 and a communication unit 336. FIG. 10 illustrates a configuration of the terminal device 400 for a hospital. The terminal device 400 for a hospital includes an input unit 410, a display unit 412, a storage unit 414, a controller 416, and a communication unit 418. Here, configurations of the call station 100, the vehicle 200, the management device 300, and the terminal device 400 for a hospital illustrated in FIGS. 7 to 10 will be described in (2.1) Call Processing, (2.2) Forward Path Moving Processing, (2.3) Movement Stop Processing (2.4) Examination Processing During Movement (2.5) Moving Processing on the Way, and (2.6) Return Path Moving Processing.

(2.1) Call Processing

Figure 11:
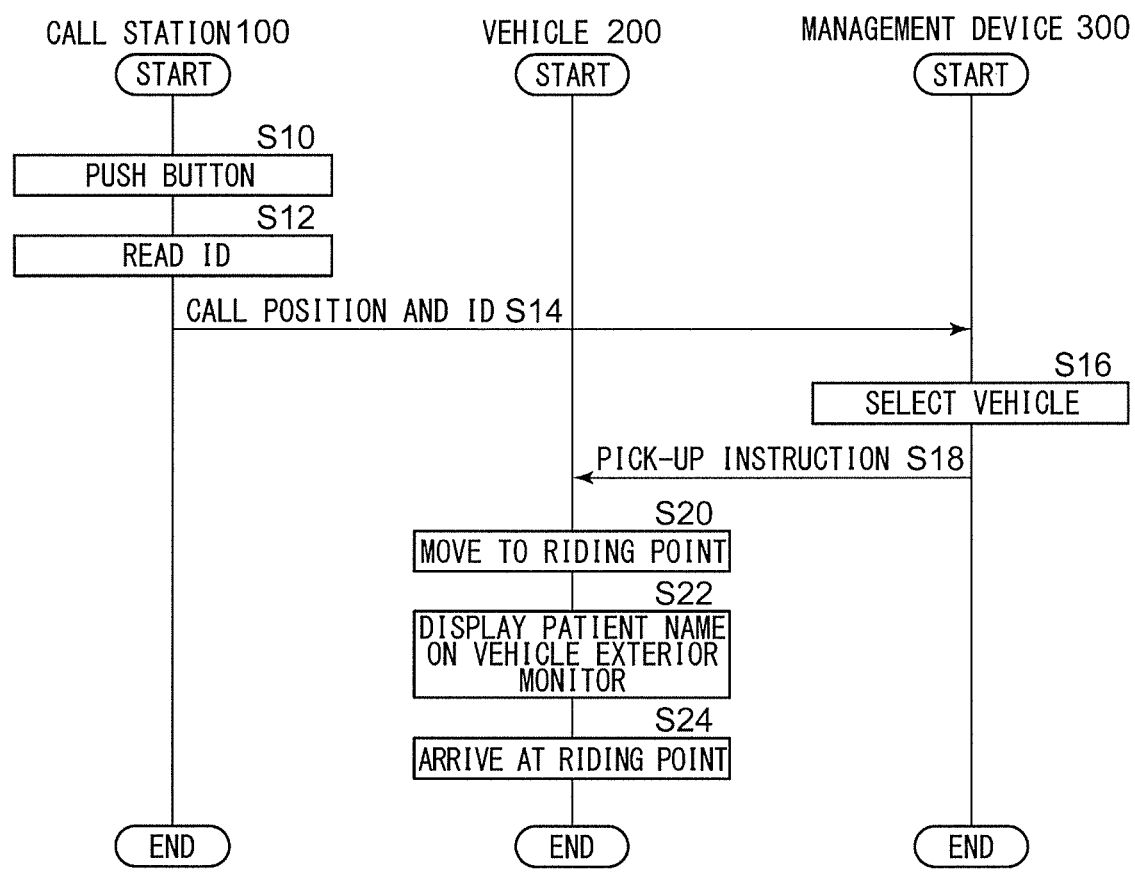
FIG. 11 is a sequence diagram illustrating a call procedure by the automatic carrier system described in FIG. 2.

FIG. 11 is a sequence diagram illustrating a call procedure by the automatic carrier system 1000. The call processing is processing to call the vehicle 200 from the call station 100 by a patient. In step S10, the button 110 of the call station 100 is pushed by a patient, and in step S12, the ID reader 112 reads a patient ID input by the patient. When the controller 118 detects that the button 110 is pushed, the controller 118 obtains the patient ID read by the ID reader 112. The controller 118 causes the communication unit 120 to send a combination of information on a position where the call station 100 is disposed (hereinafter called "a call position") and a patient ID. In step S14, the communication unit 120 sends a combination of the call position and the patient ID to the management device 300.

The communication unit 336 of the management device 300 receives the combination of the call position and the patient ID from the call station 100. The controller 334 outputs the combination of the call position and the patient ID to the management unit 324. The management unit 324 periodically receives position information of each vehicle 200 and manages a traveling state of each vehicle 200. The traveling state also includes information whether the vehicle 200 is used by a patient. Further, the management unit 324 manages information on a patient (hereinafter called "patient information") and information on a registration of the patient (hereinafter called "registration information"). In step S16, when the management unit 324 receives the combination of the call position and the patient ID, the management unit 324 selects a vacant vehicle 200 near the call position. In addition, the management unit 324 obtains patient information corresponding to the patient ID. The controller 334 generates a pick-up instruction including a call position, a patient ID, and patient information. In step S18, the communication unit 336 sends the pick-up instruction addressed to an ID of the vehicle 200 (hereinafter called "a vehicle ID") selected by the management unit 324.

The communication unit 532 of the terminal device 500 for a vehicle mounted in the vehicle 200 of the addressed vehicle ID receives the pick-up instruction. The controller 534 instructs, to the automatic driving control device 220, movement to the call position included in the pick-up instruction. In step S20, the automatic driving control device 220 moves the vehicle 200 toward a riding position which is the call position received from the controller 534. In such a case, the position sensor 222 obtains position information of the vehicle 200 and outputs the information to the automatic driving control device 220, and the radar 224 detects obstacle information around the vehicle 200 and outputs the information to the automatic driving control device 220. The automatic driving control device 220 uses the position information from the position sensor 222 and the obstacle information from the radar 224 and causes the vehicle 200 to automatically travel by referring to map information stored in the map storage 226. A known technique may be used for automatic traveling, and therefore a description will be omitted.

The controller 534 extracts a patient name from patient information included in the pick-up instruction. In step S22, the vehicle exterior monitor 526 displays a patient name. In step S24, the vehicle 200 arrives at a riding point by automatic traveling by the automatic driving control device 220. A patient recognizes the vehicle 200 to ride by confirming a patient name displayed on the vehicle exterior monitor 526 of the vehicle 200.

(2.2) Forward Path Moving Processing

Figure 12:
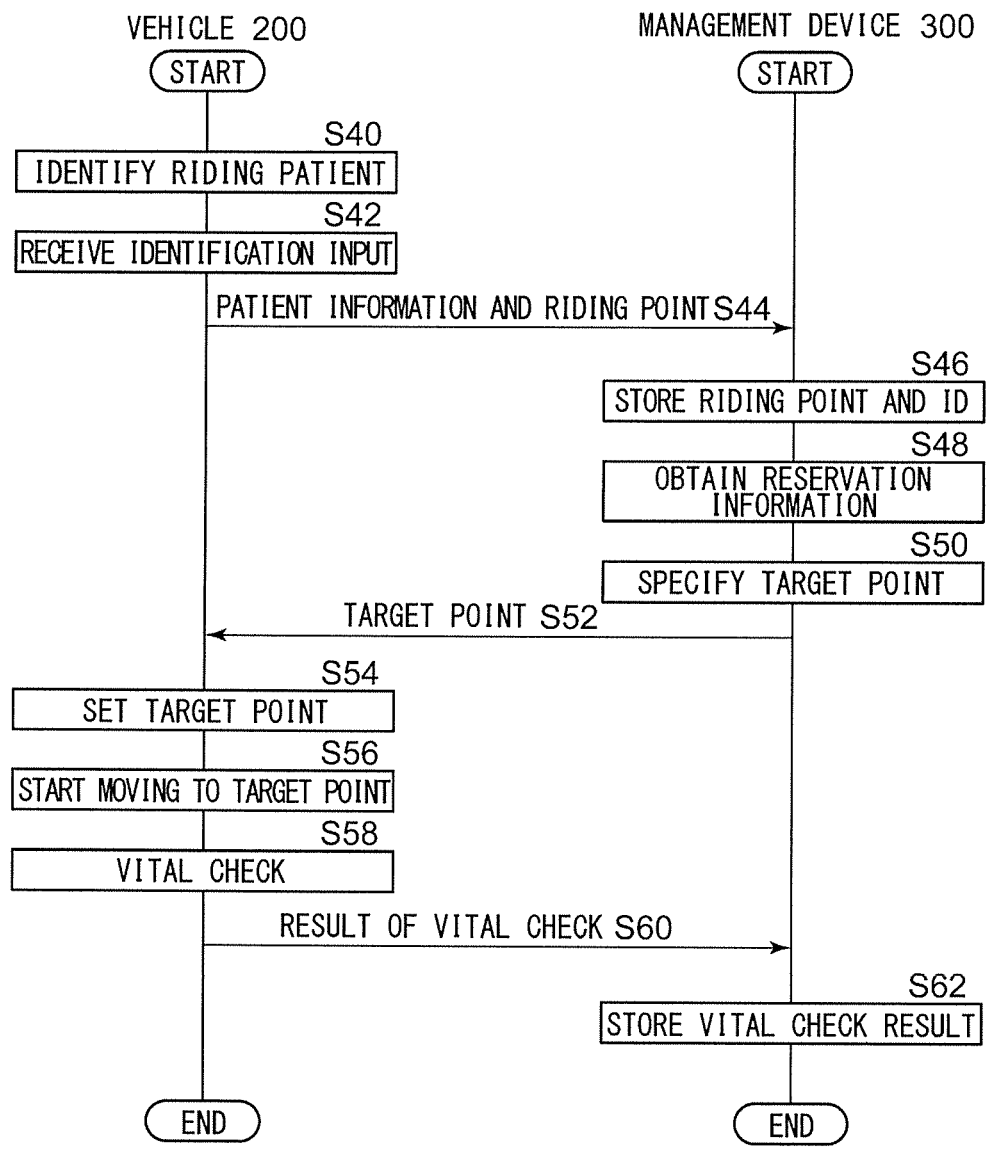
FIG. 12 is a sequence diagram illustrating a forward path movement procedure by the automatic carrier system described in FIG. 2.

FIG. 12 is a sequence diagram illustrating a forward path moving procedure by the automatic carrier system 1000. The forward path moving processing follows the call processing and is processing to move the vehicle 200 carrying a patient from a riding position to a target point. The ID reader 510 reads a patient ID input by a patient. The controller 534 obtains the patient ID read by the ID reader 510. In step S40, the controller 534 compares the obtained patient ID and a patient ID included in a pick-up instruction and identifies a riding patient when both coincide. A patient is not necessarily identified by input of a patient ID and may be identified by face authentication, fingerprint authentication, and other biometrics authentication. The controller 534 displays an identified result on the in-vehicle monitor 524. In step S42, the input unit 522 receives an input for identification from a patient. The controller 534 receives the identification input and outputs patient information and a riding point included in a pick-up instruction to the communication unit 532. In step S44, the communication unit 532 sends the patient information and the riding point to the management device 300.

The communication unit 336 of the management device 300 receives the patient information and the riding point. In step S46, the controller 334 causes the storage 530 to store a corresponding relation between a patient ID in the patient information and the riding point. The controller 334 outputs the patient information to the management unit 324. The management unit 324 manages registration information corresponding to the patient information and, in step S48, obtains registration information corresponding to the received patient information. The registration information indicates a registered examination room and a registered inspection room with registration times. In step S50, the controller 334 specifies a target point in any of the examination room and the inspection room included in the registration information. In step S52, the communication unit 336 sends the target point to the vehicle 200. Accordingly, the controller 334 automatically moves the vehicle 200 carrying a patient along a forward path from a riding point to a target point along.

The communication unit 532 of the terminal device 500 for a vehicle mounted in the vehicle 200 receives a target point. The controller 534 outputs the target point to the automatic driving control device 220. In step S54, the automatic driving control device 220 sets the target point received from the controller 534. Further, in step S56, the automatic driving control device 220 causes the vehicle 200 to automatically travel to the target point. The measurement unit 528 includes a scale, a sphygmomanometer, a thermometer, and a heartbeat meter. In step S58, vital checks of a patient are performed during automatic traveling of the vehicle 200. The controller 534 receives a measurement result in the measurement unit 528 as a result of the vital checks. In step S60, the communication unit 532 sends the vital check result and a patient ID to the management device 300 when the automatic driving control device 220 causes the vehicle 200 to automatically travel. The vital check result is also information regarding a patient riding in the vehicle 200. In step S62, the communication unit 336 of the management device 300 receives the vital check result and the patient ID. The controller 334 stores combination of the vital check result and the patient ID in the storage 316.

(2.3) Movement Stop Processing

Figure 13:
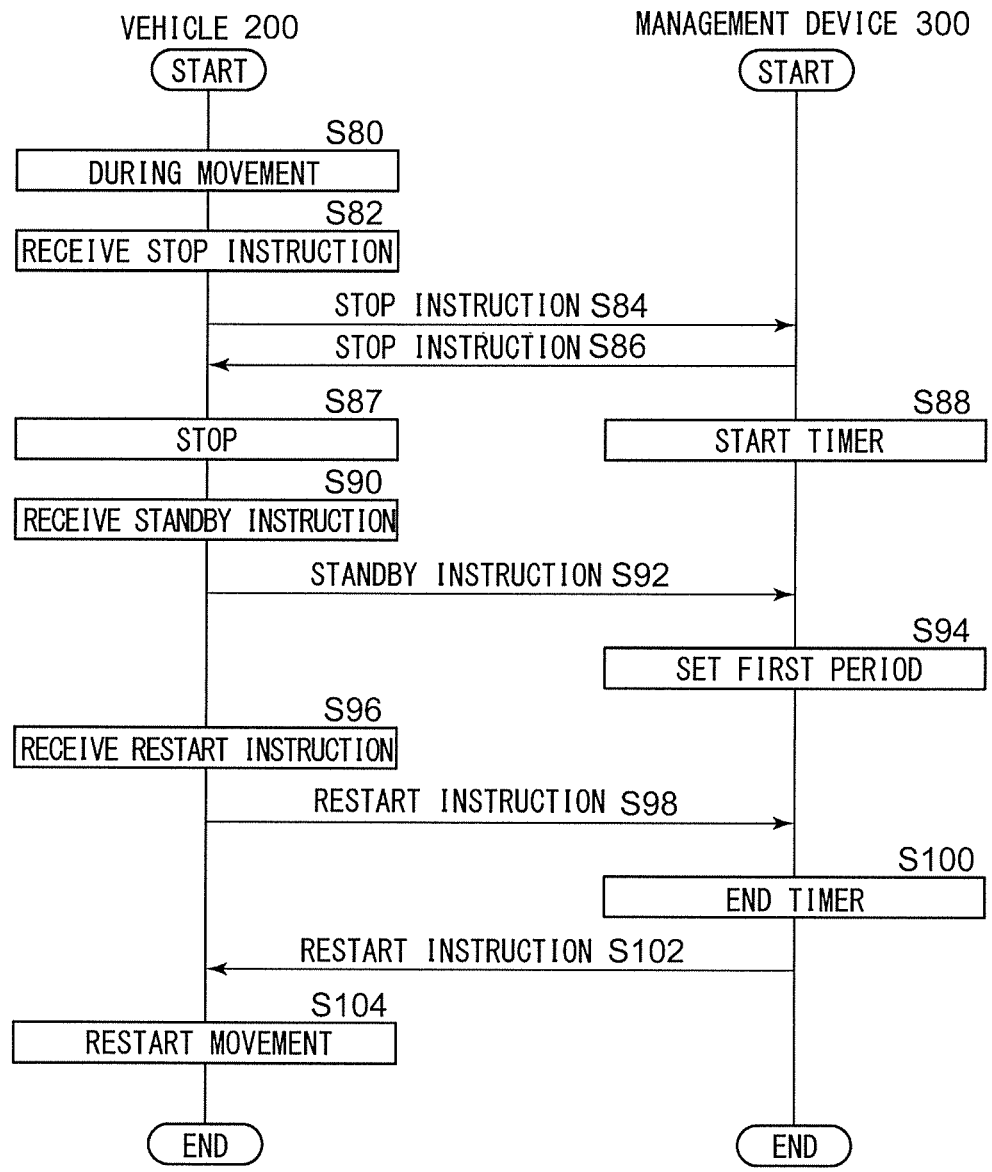
FIG. 13 is a sequence diagram illustrating a movement stop procedure by the automatic carrier system described in FIG. 2.

FIG. 13 is a sequence diagram illustrating a movement stop procedure by the automatic carrier system 1000. The movement stop processing is processing to stop the vehicle 200 by an instruction from a patient riding in the vehicle 200 while the vehicle 200 automatically travels. This processing is performed, for example, in the case where a patient temporarily gets off the vehicle to stop for such as a toilet and a store. A stop instruction includes a stop on the spot and also includes a stop after the vehicle moves to such as a toilet. In step S80, the vehicle 200 is automatically moved by the automatic driving control device 220. In step S82, the controller 534 receives a stop instruction when a patient inputs the instruction to the input unit 522 of the terminal device 500 for a vehicle mounted in the vehicle 200. In step S84, the communication unit 532 sends the stop instruction to the management device 300.

The communication unit 336 of the management device 300 receives the stop instruction. The first receiver 312 receives the stop instruction while the vehicle 200 is automatically moved to a target point. In step S86, the controller 334 causes the communication unit 336 to send the stop instruction addressed to the vehicle 200. Specifically, the controller 334 stops automatic traveling of the vehicle 200 when the first receiver 312 receives the stop instruction. The communication unit 532 of the terminal device 500 for a vehicle mounted in the vehicle 200 receives the stop instruction. In step S87, the controller 534 outputs the stop instruction to the automatic driving control device 220, and the automatic driving control device 220 stops the vehicle 200. On the other hand, in step S88, the controller 334 of the management device 300 starts a timer. At this time, the timer is set to a second period.

In step S90, when the hold button 514 of the terminal device 500 for a vehicle mounted in the vehicle 200 is pushed by a patient, the controller 534 receives a standby instruction. Here, the patient temporarily gets off the vehicle 200 to stop by such as a toilet and a store. The patient may temporarily get off the vehicle 200 and stop by such as a toilet and a store without pushing the hold button 514 after step S87. In step S92, the communication unit 532 sends a standby instruction to the management device 300. The communication unit 336 of the management device 300 receives the standby instruction. The first receiver 312 receives the standby instruction following a stop instruction. In step S94, the controller 334 changes a timer period from the second period to a first period when the first receiver 312 receives the standby instruction. The first period is longer than the second period, and therefore, this means that the timer period is extended. In the case where the first receiver 312 does not receive a standby instruction, the timer period is still the second period.

Before the first period or the second period is expired, a patient returns to the vehicle 200. In step S96, the controller 534 receives a restart instruction when a patient inputs the restart instruction to the input unit 522 of the terminal device 500 for a vehicle mounted in the vehicle 200. In this case, the patient may be identified. In step S98, the communication unit 532 sends the restart instruction to the management device 300. The communication unit 336 of the management device 300 receives the restart instruction. The second receiver 314 receives the instruction to restart automatic traveling of the vehicle 200 after the first receiver 312 receives a stop instruction. In step S100, the controller 334 ends a timer. In step S102, the controller 334 causes the communication unit 336 to send the restart instruction addressed to the vehicle 200. Specifically, the controller 334 restarts automatic traveling of the vehicle 200 when the second receiver 314 receives the restart instruction. The communication unit 532 of the terminal device 500 for a vehicle mounted in the vehicle 200 receives the restart instruction. In step S104, the controller 534 outputs the restart instruction to the automatic driving control device 220, and the automatic driving control device 220 restarts movement of the vehicle 200.

The controller 334 of the management device 300 stops automatic traveling of the vehicle 200 toward a target point in the case where the first receiver 312 receives a standby instruction after receiving a stop instruction, and the second receiver 314 does not receive a restart instruction in the first period. Further, the controller 334 stops automatic traveling of the vehicle 200 toward a target point in the case where the first receiver 312 does not receive a standby instruction after receiving a stop instruction, and the second receiver 314 does not receive a restart instruction in the second period. Consequently, the vehicle 200 finishes a mode to carry a specific patient from a state to carry the patient to a target point and changes to a mode to carry and pick up a next patient. Subsequently, the controller 334 causes the vehicle 200 to automatically travel to a new target point. Therefore, the controller 334 sends the new target point to the vehicle 200 via the communication unit 336.

(2.4) Examination Processing During Movement

Figure 14:
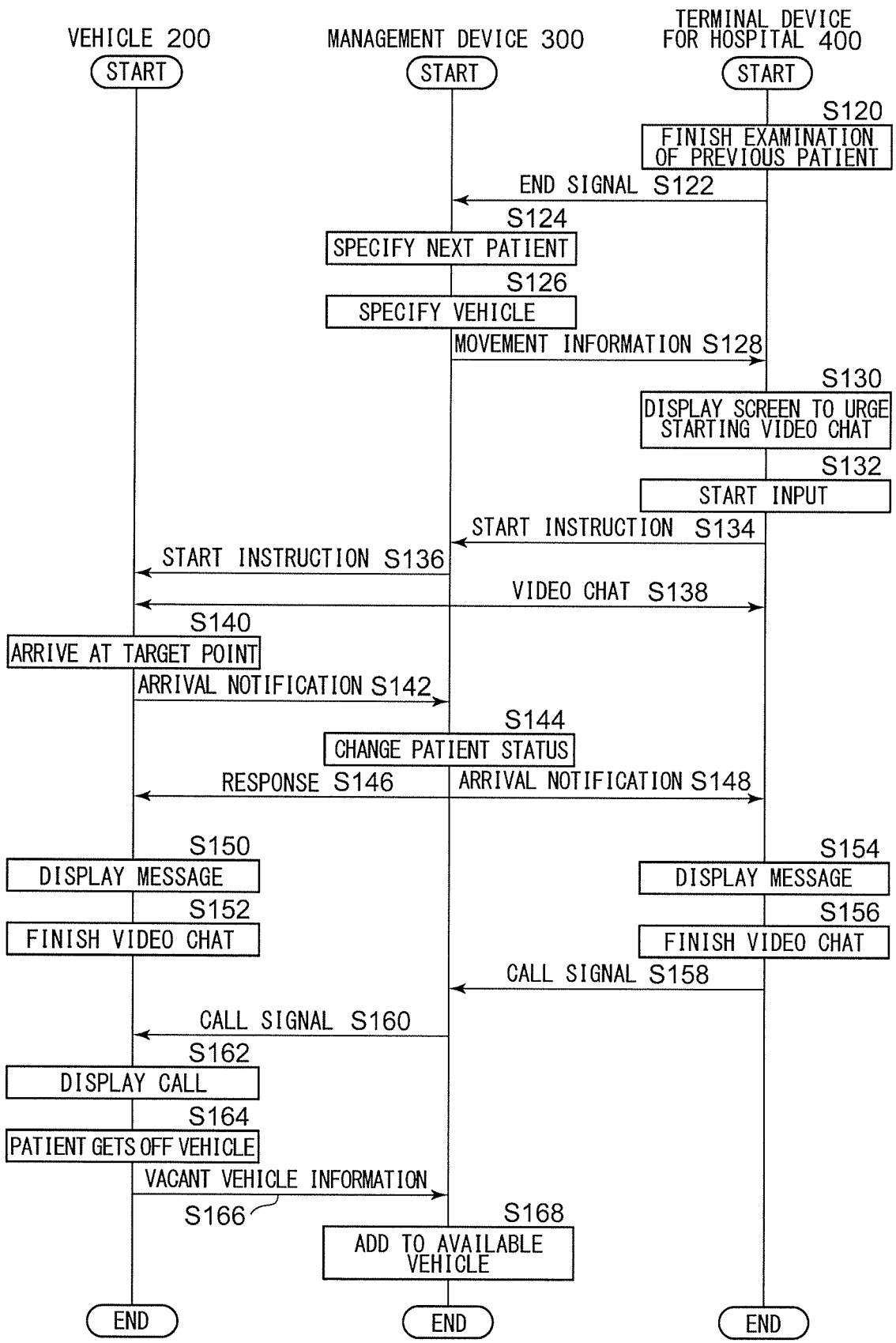
FIG. 14 is a sequence diagram illustrating an examination procedure during movement by the automatic carrier system described in FIG. 2.

FIG. 14 is a sequence diagram illustrating an examination procedure during movement by the automatic carrier system 1000. An examination processing during movement is processing to examine a patient in the vehicle 200 on the way to a target point. A doctor for the examination ends the examination of a previous patient. In step S120, the controller 416 receives end of an examination of a previous patient when a doctor inputs the end of the examination to the input unit 410 of the terminal device 400 for a hospital. When the controller 416 receives the end of the examination of a previous patient, the controller 416 generates an end signal including information to identify a doctor (hereinafter called "a doctor ID") and a patient ID of the previous patient. In step S122, the communication unit 418 sends the end signal to the management device 300.

The communication unit 336 of the management device 300 receives the end signal. The controller 334 outputs the end signal to the management unit 324. Registration information managed in the management unit 324 corresponds to each doctor. In step S124, the management unit 324 extracts a doctor ID and a patient ID from the end signal and specifies, from the registration information, a patient ID of a patient to be examined next in the extracted patient ID which is a patient ID corresponding to the doctor ID. Further, in step S126, the management unit 324 specifies a vehicle ID corresponding to the specified patient ID. This means that a doctor specifies the vehicle 200 carrying a patient to be examined next. The communication unit 336 generates movement information including a patient ID and a vehicle ID specified by the management unit 324. In step S128, the communication unit 336 sends the movement information to the terminal device 400 for a hospital The communication unit 418 of the terminal device 400 for a hospital receives movement information. In step S130, the controller 416 causes the display unit 412 to display a screen to urge start of a video chat with a patient of the patient ID included in the movement information when the patient is carried. Therefore, the movement information is an instruction to display the screen. When the patient is not being carried and arrives, steps until step S140 to be described later can be skipped. In step S132, the controller 416 receives a start input when a doctor inputs start of a video chat to the input unit 410 of the terminal device 400 for a hospital. The controller 416 generates a start instruction including a patient ID, a vehicle ID, and a doctor ID when receiving the start input. In step S134, the communication unit 418 sends the start instruction to the management device 300. The communication unit 336 of the management device 300 receives the start instruction. In step S136, the controller 334 causes the communication unit 336 to send the start instruction addressed to the vehicle 200.

The communication unit 532 of the terminal device 500 for a vehicle mounted in the vehicle 200 receives the start instruction. Consequently, in step S138, a video chat between the terminal device 500 for a vehicle and the terminal device 400 for a hospital is started. Specifically, the controller 334 of the management device 300 controls a video chat between the terminal device 500 for a vehicle and the terminal device 400 for a hospital. A communication between the terminal device 500 for a vehicle and the terminal device 400 for a hospital is not limited to a video chat and may be a voice communication. Even by the video chat and by the voice communication, a speech communication between a patient and a doctor is performed. Consequently, a doctor can examine a patient during movement in the vehicle 200. The microphone 516, the speaker 518, the camera 520, and the in-vehicle monitor 524 of the terminal device 500 for a vehicle are used for a video chat. Although not illustrated in FIG. 10, these configurations are included in the terminal device 400 for a hospital.

In step S140, based on position information obtained by the position sensor 222 of the vehicle 200, the automatic driving control device 220 detects arrival at a target point. The controller 534 generates an arrival notification indicating arrival at a target point. The arrival notification includes a vehicle ID and a patient ID. In step S142, the communication unit 532 sends the arrival notification to the management device 300. The communication unit 336 of the management device 300 receives the arrival notification.

When receiving the arrival notification, the detector 310 detects that the terminal device 500 for a vehicle moves and arrives at a target point. In step S144, from the vehicle ID and the patient ID included in the arrival notification, the management unit 324 changes a patient state corresponding to the patient ID to an examination possible state. Accordingly, in step S146, the controller 334 causes the communication unit 336 to send a response addressed to the vehicle 200. Further, in step S148, the controller 334 causes the communication unit 336 to send an arrival notification addressed to the terminal device 400 for a hospital.

The communication unit 532 of the terminal device 500 for a vehicle receives the response. In step S150, the controller 534 displays a message to notify end of a video chat on the in-vehicle monitor 524. Then, in step S152, the controller 534 ends a video chat. On the other hand, the communication unit 418 of the terminal device 400 for a hospital receives an arrival notification. In step S154, the controller 416 displays a message to notify end of a video chat on the display unit 412. Then, in step S156, the controller 416 finishes a video chat. That is, the controller 334 of the management device 300 ends a video chat between the terminal device 500 for a vehicle and the terminal device 400 for a hospital after each of the terminal device 500 for a vehicle and the terminal device 400 for a hospital outputs a message. In this manner, a video chat is finished at a timing that the vehicle 200 arrives at a target point even if an examination of a patient by a doctor is not finished. In another embodiment, an arrival is notified to a doctor, and a screen to urge to finish a video chat and call the patient in an examination room is displayed on the terminal device 400 for a hospital, and step S156 in which a video chat is finished in accordance with an instruction of the doctor and S158 for calling may by performed.

When a doctor inputs a call for a patient to the input unit 410 of the terminal device 400 for a hospital, the controller 416 receives the call for a patient. When receiving the call for a patient, the controller 416 generates a call signal including a patient ID, a vehicle ID, and a doctor ID. In step S158, the communication unit 418 sends the call signal to the management device 300. The communication unit 336 of the management device 300 receives the call signal. In step S160, the controller 334 causes the communication unit 336 to send the call signal addressed to the vehicle 200.

The communication unit 532 of the terminal device 500 for a vehicle mounted in the vehicle 200 receives the call signal. In step S162, the controller 534 displays a call in response to the call signal on the in-vehicle monitor 524. In step S164, a patient gets off the vehicle 200. A patient enters in an examination room and receives an examination continued from a video chat by a doctor. Then, the controller 534 generates vacancy information including a vehicle ID. The vacancy information is information to indicate that the vehicle 200 is vacant. In step S166, the communication unit 532 sends the vacancy information to the management device 300. The communication unit 336 of the management device 300 receives the vacancy information. In step S168, the management unit 324 additionally registers the vehicle 200 of the vehicle ID included in the vacancy information as an available vehicle 200.

(2.5) Moving Processing on the Way

Figure 15:
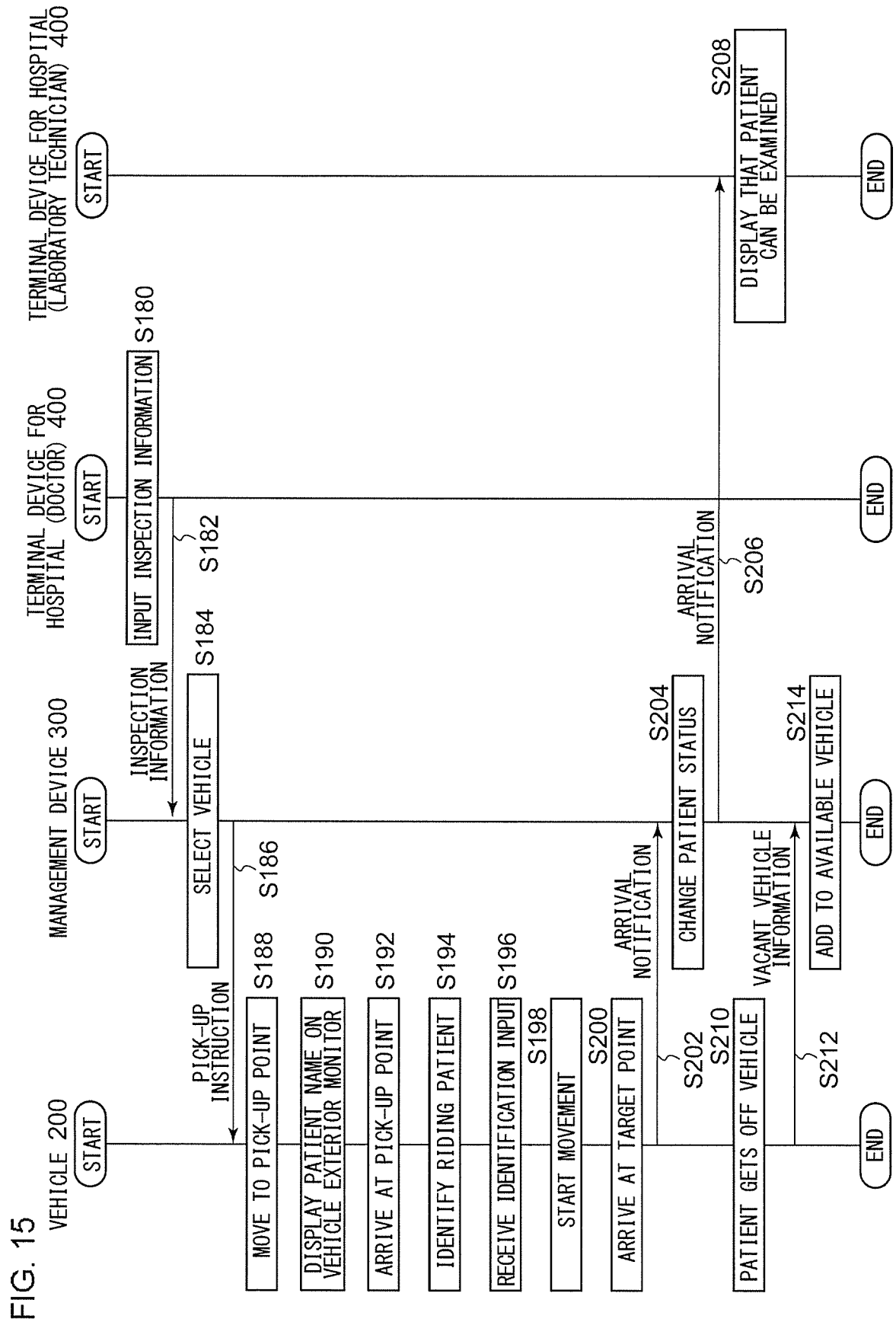
FIG. 15 is a sequence diagram illustrating a movement procedure on the way by the automatic carrier system described in FIG. 2.

FIG. 15 is a sequence diagram illustrating a movement procedure on the way by the automatic carrier system 1000. The moving processing on the way is processing to move to another room in the hospital building 910. For example, the processing is to move a patient from an examination room to an inspection room in the case where the patient has an inspection after an examination. This is caused when a doctor determines as a result of an examination that a patient needs an inspection. In step S180, by inputting inspection information to the input unit 410 of the terminal device 400 for a hospital to be used by a doctor, the controller 416 receives the inspection information. The inspection information includes a patient ID and an information on an inspection room. In the inspection room, for example, inspections by X-rays and magnetic resonance imaging (MRI) are performed. In step S182, the communication unit 418 sends the inspection information to the management device 300. In the case where an examination of a patient is finished, and the patient does not have an inspection next, the inspection information may only include a patient ID.

The communication unit 336 of the management device 300 receives the inspection information. The controller 334 outputs the inspection information to the management unit 324. The management unit 324 extracts a patient ID from the inspection information and specifies an examination room in which a patient is examined from a state corresponding to the patient ID. In step S184, the management unit 324 selects a vacant vehicle 200 near the specified examination room. The vehicle 200 may be different from the vehicle 200 used heretofore by the patient. Further, the management unit 324 generates a pick-up instruction including a pick-up point which is a specified examination room, a target point which is an inspection room, a patient ID, and patient information. In step S186, the communication unit 336 sends the pick-up instruction addressed to a vehicle ID of the vehicle 200 selected by the management unit 324.

The communication unit 532 of the terminal device 500 for a vehicle mounted in the vehicle 200 of the addressed vehicle ID receives the pick-up instruction. The controller 534 instructs, to the automatic driving control device 220, movement to a pick-up position included in the pick-up instruction. In step S188, the automatic driving control device 220 moves the vehicle 200 to the pick-up position received from the controller 534. The controller 534 extracts a patient name from patient information included in the pick-up instruction. In step S190, the vehicle exterior monitor 526 displays a patient name. In step S192, the vehicle 200 arrives at the pick-up point by automatic traveling by the automatic driving control device 220. A patient recognizes the vehicle 200 to ride by confirming a patient name displayed on the vehicle exterior monitor 526 of the vehicle 200.

The ID reader 510 reads a patient ID input by a patient. The controller 534 obtains the patient ID read by the ID reader 510. In step S194, the controller 534 compares the obtained patient ID and a patient ID included in a pick-up instruction and identifies a riding patient when both coincide. The controller 534 displays an identified result on the in-vehicle monitor 524. In step S196, the input unit 522 receives an input for identification from a patient. When receiving an input for identification from a patient, the controller 534 sets a target point to the automatic driving control device 220. Subsequently, in step S198, the automatic driving control device 220 causes the vehicle 200 to automatically travel toward a target point. In such a case, after the vehicle 200 travels to the target point, an advance preparation in accordance with contents to be performed at the target point may be performed in the vehicle 200. For example, in accordance with contents of an inspection, a video explaining a method for the inspection is displayed on the in-vehicle monitor 524. Consequently, a time for explanation by a laboratory technician can be omitted.

In step S200, based on position information obtained by the position sensor 222 of the vehicle 200, the automatic driving control device 220 detects that the vehicle 200 arrives at a target point. The controller 534 generates an arrival notification indicating arrival at a target point. In step S202, the communication unit 532 sends the arrival notification to the management device 300. The communication unit 336 of the management device 300 receives the arrival notification. In step S204, from the vehicle ID and the patient ID included in the arrival notification, the management unit 324 changes a patient state corresponding to the patient ID to an examination possible state. In step S206, the controller 334 causes the communication unit 336 to send an arrival notification addressed to the terminal device 400 for a hospital used by a laboratory technician.

The communication unit 418 of the terminal device 400 for a hospital used by a laboratory technician receives the arrival notification. In step S208, the controller 416 causes the display unit 412 to display that a patient can be examined. In step S210, a patient gets off the vehicle 200. The patient enters in an inspection room and is examined by a laboratory technician. Then, the controller 534 generates vacancy information including a vehicle ID. In step S212, the communication unit 532 sends the vacancy information to the management device 300. The communication unit 336 of the management device 300 receives the vacancy information. In step S214, the management unit 324 additionally registers the vehicle 200 of the vehicle ID included in the vacancy information as an available vehicle 200.

(2.6) Return Path Moving Processing

Figure 16:
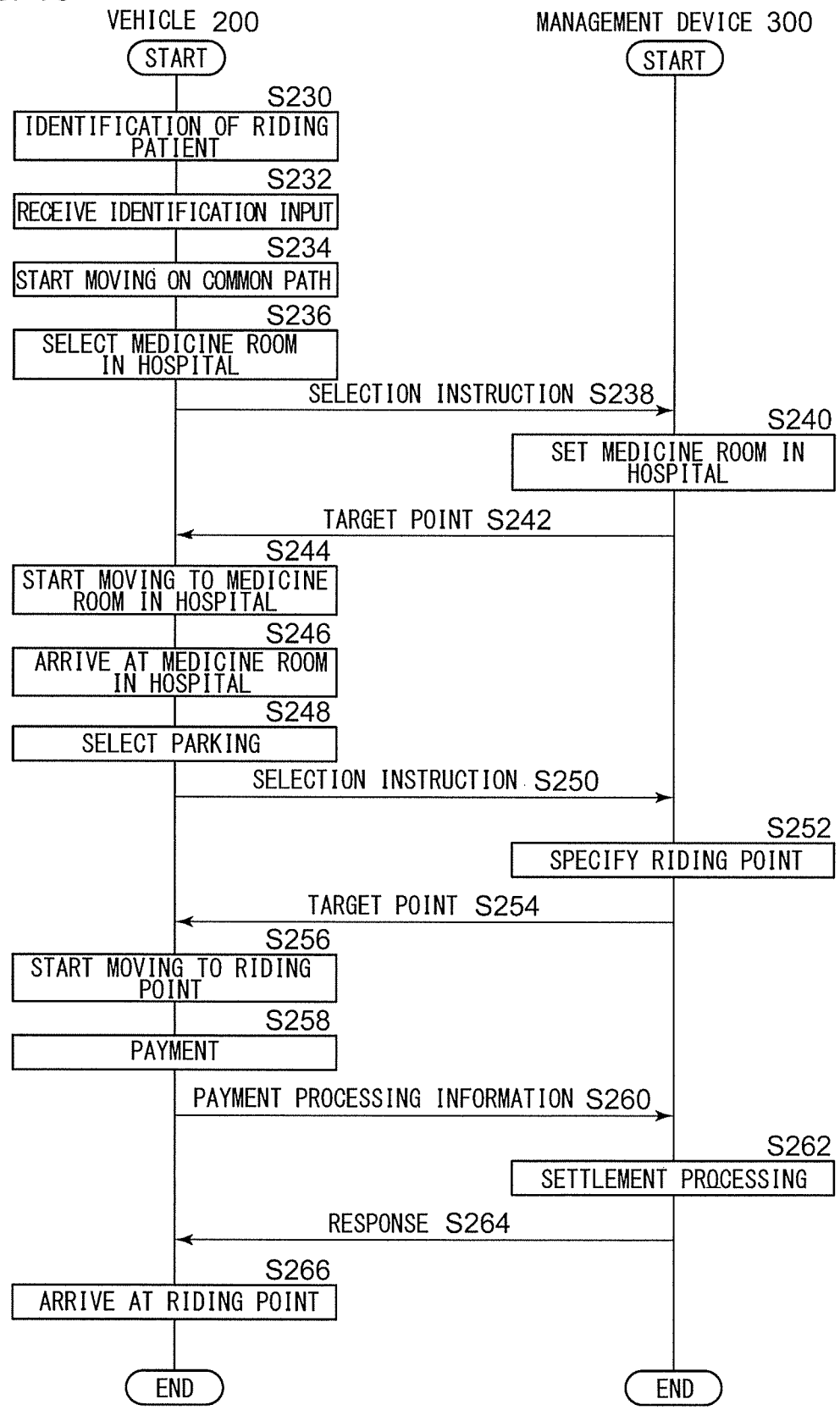
FIG. 16 is a sequence diagram illustrating a return path movement procedure by the automatic carrier system described in FIG. 2.

FIG. 16 is a sequence diagram illustrating a return path moving procedure by the automatic carrier system 1000. The return path moving processing is processing to return a patient who has finished every examinations and inspections scheduled in the day to a riding point, and the finish is confirmed by the management device 300. Here, a patient recognizes whether to stop at a medicine room in a hospital or to go for payment. The patient rides in the vehicle. The ID reader 510 reads a patient ID input by a patient. The controller 534 obtains the patient ID read by the ID reader 510. In step S230, the controller 534 compares the obtained patient ID and a patient ID included in a pick-up instruction and identifies a riding patient when both coincide. The controller 534 displays an identified result on the in-vehicle monitor 524. In step S232, the input unit 522 receives an input for identification from a patient.

When receiving an input for identification from a patient, the controller 534 instructs the automatic driving control device 220 to start movement. Here, the controller 534 recognizes from a notification from the management device 300 that the patient finishes an examination and an inspection, but does not recognize whether to stop at a medicine room in a hospital, go for payment, or go to the parking 920. Therefore, the setting unit 318 of the management device 300 sets the medicine room in a hospital, the payment window, and the parking 920 as candidates of target points, and the controller 334 preliminary instructs the vehicle 200 to move along a common path to a plurality of the target point candidates set by the setting unit 318. The common path to a plurality of the candidates is common path toward the medicine room in a hospital, the payment window, and the parking 920. In step S234, the automatic driving control device 220 causes the vehicle 200 to automatically travel along the common path in accordance with an instruction from the controller 334.

The controller 534 displays a screen on the in-vehicle monitor 524 to make a patient select the medicine room in a hospital, the payment window, or the parking 920 as a destination. In step S236, the input unit 522 receives a selection of the medicine room in a hospital from a user. The controller 534 generates a selection instruction indicating that the medicine room in a hospital is selected. In step S238, the communication unit 532 sends the selection instruction to the management device 300. The communication unit 336 of the management device 300 receives the selection instruction. The third receiver 320 receives the selection instruction while the controller 334 causes the vehicle 200 to automatically travel. The selection instruction is an instruction to select any of a plurality of target point candidates set by the setting unit 318, as a target point. In step S240, the controller 334 sets the selected medicine room as a target point in the case where the third receiver 320 receives an instruction. In step S242, the communication unit 336 sends, to the vehicle 200, the target point set by the controller 334.

The communication unit 532 of the terminal device 500 for a vehicle mounted in the vehicle 200 receives a target point. The controller 534 outputs the target point to the automatic driving control device 220. In step S244, the automatic driving control device 220 causes the vehicle 200 to automatically travel to the medicine room in a hospital which is the target point. In step S246, based on position information obtained by the position sensor 222 of the vehicle 200, the automatic driving control device 220 detects that the vehicle 200 arrives at the medicine room in a hospital which is the target point. Here, an arrival notification may be sent from the vehicle 200 to the management device 300. A patient returns to the vehicle 200 after getting off the vehicle 200 and stopping at the medicine room in a hospital. Subsequently, the automatic driving control device 220 causes the vehicle 200 automatically travels. In such a case, the controller 334 may set a common path to the payment window and the parking 920 other than the medicine room in a hospital.

The controller 534 displays a screen on the in-vehicle monitor 524 to make a patient select the payment window, or the parking 920 as a destination. In step S248, the input unit 522 receives that the parking 920 is selected from a user. The controller 534 generates a selection instruction indicating that the parking 920 is selected. In step S250, the communication unit 532 sends the selection instruction to the management device 300. The communication unit 336 of the management device 300 receives the selection instruction, and the third receiver 320 receives the selection instruction. In step S252, the controller 334 specifies a riding point of a passenger from a correspondence relation stored in the storage 316 based on a patient ID included in the selection instruction. In step S254, the communication unit 336 sends the riding point as a target point to the vehicle 200. This corresponds that the controller 334 sets the obtained riding point as an alighting point on a return path to the vehicle 200. Here, in the case where the vehicle 200 does not stop at an medicine room in a hospital and a payment window, a return path is started from an examination room or an inspection room. However, in the case where the vehicle 200 does not stop at the medicine room or the payment hospital, the return path is started from the medicine room or the payment window at which the vehicle 200 has stopped.

The communication unit 532 of the terminal device 500 for a vehicle mounted in the vehicle 200 receives a target point. The controller 534 outputs the target point to the automatic driving control device 220. In step S256, the automatic driving control device 220 causes the vehicle 200 to start movement to a riding point which is a target point and automatically travel along a return path. The controller 534 displays a screen on the in-vehicle monitor 524 to perform payment by credit card by a patient. A credit card is inserted into the card reader 512. The card reader 512 obtains credit card information and output to the controller 534. In step S258, the controller 334 performs the payment by generating payment information based on the credit card information. In step S260, the communication unit 532 sends the payment information to the management device 300.

The communication unit 336 of the management device 300 receives the payment information. The controller 334 settles the payment by accessing to a server of a card company connected to the outside. In step S264, the communication unit 336 sends a response indicating that the payment is settled by the controller 334 to the vehicle 200. The vehicle 200 is traveling during the payment, and the communication unit 532 in the terminal device 500 for a vehicle mounted in the vehicle 200 receives the response. Further, while the vehicle 200 is traveling toward a riding point, the in-vehicle monitor 524 may display a video to review contents of a medicine and how to take the medicine. In step S266, based on position information obtained by the position sensor 222 of the vehicle 200, the automatic driving control device 220 detects that the vehicle 200 arrives at a riding point which is a target point. The vehicle 200 stops at the riding point, and a patient gets off the vehicle 200. Further, the patient rides in the automobile 930 and leaves from the parking 920.

This configuration can be realized by hardware such as a CPU, a memory, and other LSI of an arbitrary computer and can be realized by software such as a program loaded in a memory. Herein, function blocks realized by a combination of hardware and software are envisaged. Therefore, persons skilled in the art are understood that these function blocks are realized by hardware or by a combination of hardware and software.

Figure 17:
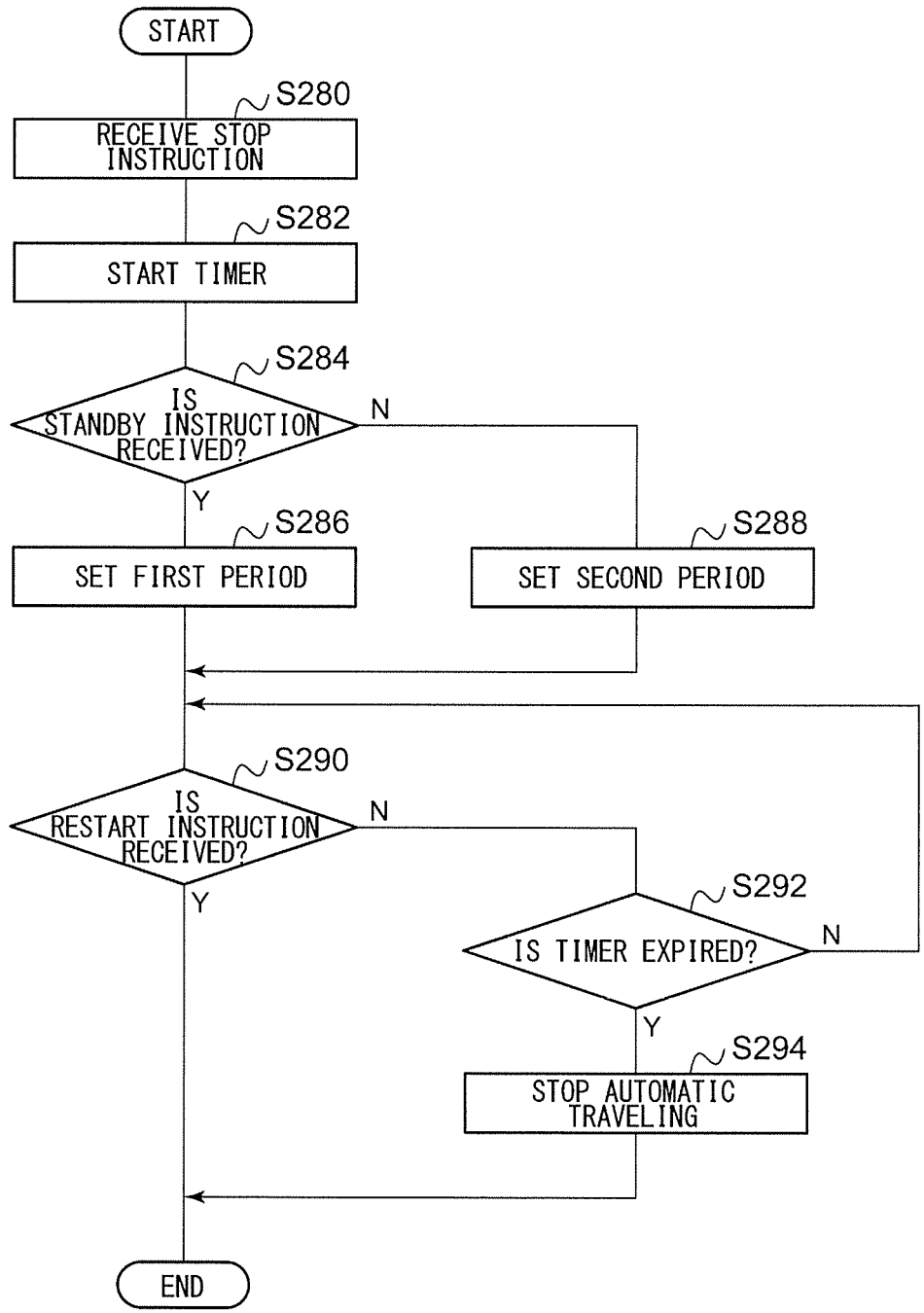
FIG. 17 is a flowchart illustrating a movement stop procedure by a management device described in FIG. 9.

An operation of the automatic carrier system 1000 having the above-described configuration will be described. FIG. 17 is a flowchart illustrating a movement stop procedure by the management device 300. This indicates an operation of the management device 300 in (2.3) Moving Stop Processing. The first receiver 312 receives a stop instruction (S280). The controller 334 starts a timer (S282). In the case where the first receiver 312 receives a standby instruction (Y in S284), the controller 334 sets a first period (S286). On the other hand, in the case where the first receiver 312 does not receive a standby instruction (N in S284), the controller 334 sets a second period (S288). In the case where the second receiver 314 does not receive a restart instruction (N in S290), processing is returned to S290 if the timer is not expired (N in S292). In the case where the timer is expired (Y in S292), the controller 334 stops automatic traveling (S294). In the case where the second receiver 314 receives a restart instruction (Y in S290), the processing is finished.

Figure 18:
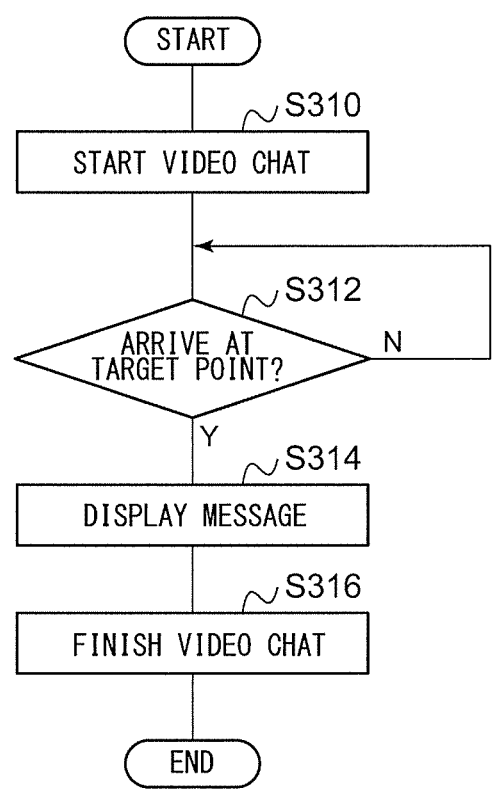
FIG. 18 is a flowchart illustrating an examination procedure during movement by the management device described in FIG. 9.

FIG. 18 is a flowchart illustrating an examination procedure during movement by the management device 300. This indicates an operation of the management device 300 in (2.4) Examination Processing During Movement The controller 334 starts a video chat between the terminal device 500 for a vehicle and the terminal device 400 for a hospital (S310). If the detector 310 does not detect arrival to a target point (N in S312), the controller 334 waits. When the detector 310 detects arrival at the target point (Y in S312), the controller 334 causes the terminal device 500 for a vehicle and the terminal device 400 for a hospital to display a message (S314) and finishes a video chat (S316).

According to the embodiment of the present invention, in the case where a vehicle arrives at a target point, a video chat between the terminal device for a vehicle and the terminal device for a hospital is finished. Therefore, the video chat is performed while moving. In addition, since the video chat is performed during movement, an examination can be started during movement. In addition, since the examination is started during movement, a time can be effectively used. In addition, since a time can be effectively used, a stay time in a hospital can be shortened. In addition, in the case where a vehicle arrives at a target point, a video chat between a terminal device for a vehicle and a terminal device for a hospital is finished, and the examination can be shifted to a face-to-face examination continued from the video chat. In addition, the communication is finished after a message is output, and therefore, finish of the video chat between a patient and a doctor can be notified in advance. In addition, since finish of a video chat between a patient and a doctor can be notified in advance, the finish of a video chat can be prepared. In addition, since the finish of a video chat is prepared, an examination can be smoothly shifted to the face-to-face examination.

In addition, a period in which a restart instruction can be received is changed according to whether a standby instruction is received. Therefore, unnecessary stop of a vehicle can be avoided. In addition, a first period is set when a standby instruction is received, and therefore it is prevented that a vehicle starts moving even when the vehicle needs to be on standby. In addition, a second period is set when a standby instruction is not received. Therefore, it is prevented that a vehicle is on standby forever. In addition, since it is prevented that a vehicle is on standby forever, it is prevented that an efficiency of operation management of a vehicle is reduced In addition, since it is prevented that the efficiency of the operation management of a vehicle is reduced, a time for waiting arrival of a vehicle can be shortened. In addition, since the time for waiting the arrival of a vehicle is shortened, a stay time in a hospital can be shortened. In addition, in the case where automatic traveling is stopped, automatic traveling toward a new target point is started. Therefore, a vehicle can be effectively used.

When a forward path is set, a corresponding relation between a riding point and a patient ID is stored, and the stored riding point is set as an alighting point on a return path. Therefore, the alighting point can be automatically acquired. In addition, since the alighting point is automatically obtained, a vehicle can arrive at the alighting point even if a patient forgets the alighting point. In addition, since a vehicle arrives at an alighting point even if a patient forgets the alighting point, it is prevented that the vehicle gets lost to find an alighting point. Since a state in which the vehicle gets lost to find an alighting point is prevented, a stay time in a hospital can be shortened. In addition, since a return path starts from a target point, a vehicle moves by the shortest route. In addition, the vehicle moves by the shortest route, a stay time in a hospital can be shortened. In addition, since a return path is started from a point different from a target point, a route can be flexibly set. In addition, the route can be flexibly set, a practicability can be improved.

In addition, before a target point is set, a vehicle is automatically moved along a common path to a plurality of target point candidates. Therefore, a stop time can be shortened. In addition, since a stop time is shortened, a stay time in a hospital can be shortened. In addition, the information on a passenger is communicated while a vehicle automatically travels, a period of automatic traveling is effectively used. In addition, since a period in which a vehicle automatic travels can be effectively used, a stay time in a hospital can be shortened. In this case, while a vehicle automatically travels, a result of vital checks is sent. Therefore, it is avoided that the result of vital checks is sent after a vehicle stops. In addition, since it is avoided that the result of vital checks is sent after a vehicle stops, a stay time in a hospital can be shortened.

An outline of the embodiment of the present invention will be described below.

(Item 1-1)

A management device, comprising:

a controller that controls communication between a movable first terminal device and a second terminal device in which a moving range is narrower than the first terminal device; and a detector that detects that the first terminal device arrives at a target point by movement, wherein in a case where the detector detects the arrival at the target point, the controller ends the communication between the first terminal device and the second terminal device.

According to this embodiment, the communication between the first terminal device and the second terminal device is ended when the first terminal device arrives at a target point, and therefore a stay time can be shortened by communication only performed during the movement.

(Item 1-2)

The management device according to item 1-1, wherein the controller controls a speech communication between the first terminal device and the second terminal device, and the controller ends the speech communication between the first terminal device and the second terminal device after causing each of the first terminal device and the second terminal device to output a message.

In this case, the communication is ended after the message is output, and therefore termination of the communication can be notified in advance.

(Item 2-1)

A control device, comprising:

a first receiver that receives a stop instruction while a vehicle automatically travels toward a target point;

a second receiver that receives an instruction to restart automatic traveling of the vehicle after the first receiver has received the stop instruction; and a controller that stops automatic traveling of the vehicle when the first receiver receives the stop instruction and restarts automatic traveling of the vehicle when the second receiver receives the restart instruction, wherein the controller (1) stops automatic traveling of a Vehicle toward a target point in a case where the first receiver also receives a standby instruction after receiving a stop instruction, and the second receiver does not receive a restart instruction during a first period, and (2) stops automatic traveling of the vehicle toward a target point in a case where the first receiver does not receive a standby instruction after receiving a stop instruction, and the second receiver does not receive a restart instruction during a second period, and in the controller, the first period is longer than the second period.

According to this embodiment, a period in which a restart instruction can be received is changed according to whether a standby instruction is received. Therefore, unnecessary stop of a vehicle can be avoided.

(Item 2-2)

The control device according to item 2-1, wherein the controller starts automatic traveling toward a new target point in a case where automatic traveling of a vehicle toward a target point is stopped.

In this case, in the case where automatic traveling is stopped, automatic traveling toward a new target point is started. Therefore, a vehicle can be effectively used.

(Item 3-1)

A management device, comprising:

a storage that stores a corresponding relation between a riding point of a passenger and identification information of the passenger; and a controller that causes a first vehicle carrying the passenger to automatically travel along a forward path from the riding point to a target point and causes a second vehicle carrying the passenger to automatically travel along a return path, wherein the controller obtains the riding point of the passenger from the corresponding relation stored in the storage based on the identification information of the passenger and sets the obtained riding point as an alighting point on the return path.

According to this embodiment, when a forward path is set, a corresponding relation between a riding point and identification information is stored, and the stored riding point is set as an alighting point on a return path. Therefore, the alighting point can be automatically obtained.

(Item 3-2)

The management device according to item 3-1, wherein a return path in the controller starts from a target point.

In this case, the return path starts from the target point. Therefore, a vehicle travels by the shortest route.

(Item 3-3)

The management device according to item 3-1, wherein, in the controller, a return path starts from a point different from a target point.

In this case, the return path starts from a point different from the target point. Therefore, a route can be flexibly set.

(Item 4-1)

A control device, comprising:

a setting unit that sets a plurality of candidate target points;

a controller that causes a vehicle to automatically travel along a common path to a plurality of the candidate target points set by the setting unit; and a receiver that receives an instruction to select a target point from any of a plurality of the candidate target points set by the setting unit while the controller causes the vehicle to automatically travel, wherein the controller causes the vehicle to automatically travel along a path to a selected target point in a case where the receiver receives the instruction.

According to this embodiment, before a target point is set, a vehicle is automatically traveled along the common path to a plurality of the candidate target points. Therefore, a stop time can be shortened.

(Item 5-1)

A control device, comprising:

a controller that causes a vehicle to automatically travel; and a communication unit that communicates information on a passenger riding in the vehicle while the controller causes the vehicle to automatically travel.

According to this embodiment, the information on a passenger is communicated while the vehicle is automatically traveled, a period of automatic traveling is effectively used.

(Item 5-2)

The control device according to item 5-1, wherein the information on a passenger in the communication unit is a result of a vital check of the passenger.

In this case, the result of a vital check is sent while a vehicle is automatically traveled. Therefore, it is avoided that the result of a vital check is sent after a vehicle stops.

(Item 6-1)

A management device, comprising:

a communication unit that receives, from a first terminal device used by a doctor, an end signal indicating that an examination of a previous patient ends; and a management unit that specifies a patient to be examined next based on the end signal received by the communication unit, wherein, in a case where the patient specified by the management unit is moving, the communication unit sends, to the first terminal device, an instruction to display a screen to urge start a call with the second terminal device used by the patient specified by the management unit.

According to this embodiment, when an examination of a previous patient ends, a call with a next patient is facilitated. Therefore, a time can be effectively used.

(Item 7-1)

A management device, comprising:

a communication unit that, in a case where a patient receives a following treatment after an examination, receives, from a terminal device used by a doctor, identification information of the patient and information including information on a room for the following treatment; and a management unit that calls a vehicle close to an examination room based on the information received by the communication unit, wherein, when the management unit calls the vehicle close to the examination room, the management unit causes the communication unit to send identification information on the patient and information on the room for a following treatment.

According to this embodiment, the communication unit sends the identification information of a patient and the information on a room for a following treatment. Therefore, the patient can be immediately carried to the room for a following treatment by the vehicle.

(Item 7-2)

The management unit according to item 7-1, wherein the following treatment is an inspection, and a room for the following treatment is an inspection room.

In this case, information on the inspection room is sent as information on the room for the following treatment. Therefore, the patient can be immediately carried to the inspection room by a vehicle.

(Item 7-3)

A management device, comprising:

a communication unit that receives information from a terminal device used by a doctor in a case where an examination of a patient ends; and a management unit that calls a vehicle close to an examination room based on the information received by the communication unit.

According to this embodiment, in a case where an examination of a patient ends, the management unit calls a vehicle close to an examination room. Therefore the patient can be immediately carried by the vehicle.

(Item 8-1)

A control device, comprising:

a controller that displays a screen to explain an inspection method on a monitor in a case where a vehicle moves toward an inspection, wherein the controller displays a screen to review contents of a medicine and how to take the medicine on the monitor in a case where a vehicle moves to a place for going home.

According to this embodiment, the explanation screen is displayed in a vehicle. Therefore, a time for explanation out of the vehicle can be shortened.

The present invention has been described above according to the embodiments. The embodiments are described as an example. A person skilled in the art understands that the embodiments can be varied by combination of each component or each processing of the embodiments, and such variation is within the scope of the present invention.

In the embodiments, the automatic carrier system 1000 is provided in the hospital 900. However, the automatic carrier system 1000 is not limited thereto, and, for example, may be provided in a facility other than the hospital 900. In this case, a patient may be called a passenger. According to the variation, the scope of applications of the embodiments can be expanded.

In the embodiments, at least a part of functions included in the management device 300 may be included in the terminal device 500 for a vehicle. The functions can be incorporated as a control device. According to the variation, degrees of freedom of the configuration can be improved.

Reference Sign List

What is claimed is:

1. A control device configured to be located in a vehicle, comprising:

a controller that causes the vehicle to automatically travel; and a communication unit that communicates information of a patient riding in the vehicle with a terminal device configured to be located in a hospital, while the controller causes the vehicle to automatically travel, wherein while the patient is in the vehicle including the control device, and the vehicle including the control device travels automatically to a destination, after the terminal device in the hospital outputs a screen suggesting start of a communication with the patient, on a display of the terminal device, when the terminal device in the hospital receives a start input of the communication with the patient in the vehicle, from an input of the terminal device, the terminal device in the hospital triggers initiation of the communication between the control device and the terminal device, and while the patient is in the vehicle including the control device, and the vehicle including the control device travels automatically to the destination, and the communication between the control device and the terminal device continues, the initiation of the communication being triggered by the terminal device in the hospital, when the vehicle including the control device arrives at the destination, the control device in the vehicle triggers termination of the communication between the control device and the terminal device, triggered to initiate by the terminal device in the hospital.

2. The control device according to claim 1, wherein the information of the patient is a result of a vital check of the patient.

3. The control device according to claim 2, wherein the information of the patient is vital information of the patient.

4. The control device according to claim 1, wherein the communication unit is further configured to communicate the information of the patient with a system management device.

5. The control device according to claim 1, wherein the communication unit is configured to receive an identification of the patient.

6. The control device according to claim 1, wherein the patient is a patient of the hospital.

7. The control device according to claim 1, wherein
the communication unit is configured to communicate with the terminal device and a system management device, and
while the communication between control device and the terminal device continues, when the system management device detects that the vehicle arrives at the destination, the system management device terminates the communication between the control device and terminal device.

8. The control device according to claim 7, wherein the system management device comprises a detector that detects that the vehicle arrives at the destination.

9. The control device according to claim 1, wherein the destination is at least one of an examination room or an inspection room in the hospital.

10. A communication management system comprising:
a terminal device configured to be located in a hospital; and
a vehicle configured to travel autonomously and communicate information of a patient riding in the vehicle while the vehicle travels autonomously, wherein
while the patient is in the vehicle and the vehicle travels automatically to a destination, after the terminal device in the hospital outputs a screen suggesting start of a communication with the patient, on a display of the terminal device, when the terminal device in the hospital receives a start input of the communication with the patient in the vehicle, from an input of the terminal device, the terminal device in the hospital triggers initiation of the communication between the vehicle and the terminal device, and while the patient is in the vehicle and the vehicle travels automatically to the destination, and the communication between the vehicle and the terminal device continues, the initiation of the communication being triggered by the terminal device in the hospital, when the vehicle arrives at the destination, the vehicle triggers termination of the communication between the vehicle and the terminal device, the initiation of the communication being triggered to initiate by the terminal device in the hospital.

11. The communication management system to claim 10, wherein the information of the patient is a result of a vital check of the patient.

12. The communication management system to claim 11, wherein the information of the patient is vital information of the patient.

13. The communication management system according to claim 10, wherein the vehicle is further configured to communicate the information of the patient with a system management device.

14. The communication management system according to claim 10, wherein the vehicle is configured to receive an identification of the patient.

15. The communication management system according to claim 10, wherein the patient is a patient of the hospital.

16. The communication management system according to claim 10, wherein
the vehicle is configured to communicate with the terminal device and a system management device, and
while the communication between vehicle and the terminal device continues, when the system management device detects that the vehicle arrives at the destination, the system management device terminates the communication between the vehicle and terminal device.

17. The communication management system according to claim 16, wherein the system management device comprises a detector that detects that the vehicle arrives at the destination.

18. The communication management system according to claim 10, wherein the destination is at least one of an examination room or an inspection room in the hospital.

* * * * *